United States Patent
Viola et al.

(10) Patent No.: US 12,109,724 B2
(45) Date of Patent: Oct. 8, 2024

(54) CHAIN SAWS, COMPONENTS FOR CHAIN SAWS, AND SYSTEMS FOR OPERATING SAWS

(71) Applicant: Chain Orthopedics, LLC, Bogota, NJ (US)

(72) Inventors: Paul Viola, Bogota, NJ (US); Ira Sanders, Oakland, NJ (US); Timothy J. Langloss, Berwyn, PA (US)

(73) Assignee: Chain Orthopedics, LLC, Bogota, NJ (US)

( * ) Notice: Subject to any disclaimer, the term of this patent is extended or adjusted under 35 U.S.C. 154(b) by 0 days.

(21) Appl. No.: 17/443,646

(22) Filed: Jul. 27, 2021

(65) Prior Publication Data

US 2022/0032489 A1 Feb. 3, 2022

Related U.S. Application Data

(60) Provisional application No. 63/209,540, filed on Jun. 11, 2021, provisional application No. 63/154,379,
(Continued)

(51) Int. Cl.
  *B27B 33/14* (2006.01)
  *B23D 57/02* (2006.01)
  (Continued)

(52) U.S. Cl.
  CPC .......... *B27B 33/142* (2013.01); *B23D 57/023* (2013.01); *B27B 17/02* (2013.01); *B27B 17/083* (2013.01)

(58) Field of Classification Search
  CPC ..... B27B 57/023; B27B 17/083; B27B 17/02; B27B 33/142
  See application file for complete search history.

(56) References Cited

U.S. PATENT DOCUMENTS

| 614,003 | A | * | 11/1898 | Johnson | ................. | B23D 53/02 |
| | | | | | | 83/831 |
| 1,178,362 | A | * | 4/1916 | Wall | ...................... | B23Q 11/02 |
| | | | | | | 83/831 |

(Continued)

FOREIGN PATENT DOCUMENTS

| CN | 1827275 A | 9/2006 |
| EP | 2990170 A1 | 3/2016 |

(Continued)

OTHER PUBLICATIONS

Bosch Media Service, "Quick, easy and powerful sawing in house and garden: New 'NanoBlade' saw from Bosch for DIY enthusiasts," Robert Bosch GmbH (https://www.bosch-presse.de/pressportal/de/en/18-volt-akku-saege-erweitert-das-programm-148813.html), 7 pages (2018).

(Continued)

*Primary Examiner* — Evan H MacFarlane
*Assistant Examiner* — Liang Dong
(74) *Attorney, Agent, or Firm* — Potomac Law Group, PLLC; Douglas E. Ringel

(57) ABSTRACT

Improved chain saws, components for chain saws, methods of making chain saws and components, and methods of using chain saws and components are disclosed. In some embodiments, a chain saw comprises a saw bar and a plurality of links, wherein a first link has a hook that engages a recess of a second link, thereby coupling the first link and the second link and allowing them to articulate without decoupling. The saw bar may have a rail, and the links may have grooves such that the links straddle and ride over the rail. The rail may have a projection and the grooves of the links may have notches accommodating the projection such that the projection prevents dislocation of the links. The links may have conical or pyramidal cutting teeth. The chain (Continued)

may be bidirectional. Robotic and automated operation of saws and other instruments are also disclosed.

23 Claims, 21 Drawing Sheets

Related U.S. Application Data filed on Feb. 26, 2021, provisional application No. 63/147,033, filed on Feb. 8, 2021, provisional application No. 63/085,290, filed on Sep. 30, 2020, provisional application No. 63/058,216, filed on Jul. 29, 2020.

(51) Int. Cl.
    *B27B 17/02* (2006.01)
    *B27B 17/08* (2006.01)

(56) References Cited

U.S. PATENT DOCUMENTS

| | | | |
|---|---|---|---|
| 2,007,806 A * | 7/1935 | Logan | E21C 25/34 |
| | | | 299/83.1 |
| 2,117,586 A * | 5/1938 | Willson | B27B 33/08 |
| | | | 83/852 |
| 2,308,847 A * | 1/1943 | Wolf | B27B 33/142 |
| | | | 83/832 |
| 2,380,753 A * | 7/1945 | Hard Af Segerstad | |
| | | | B27B 33/14 |
| | | | 30/384 |
| 2,427,580 A | 9/1947 | Stryker | |
| 2,638,944 A | 5/1953 | Woleslagle | |
| 2,649,871 A * | 8/1953 | Desbarat | B27B 17/02 |
| | | | 83/790 |
| 3,910,147 A | 10/1975 | Heyerdahl | |
| 4,316,327 A | 2/1982 | Scott et al. | |
| 4,457,307 A | 7/1984 | Stillwell | |
| 4,492,140 A | 1/1985 | Pano | |
| 4,562,761 A | 1/1986 | Alexander | |
| 4,683,659 A | 8/1987 | Wunsch et al. | |
| 4,807,366 A | 2/1989 | Masato et al. | |
| 5,209,216 A | 5/1993 | Mogi | |
| 5,226,404 A | 7/1993 | Mogi et al. | |
| 5,345,686 A | 9/1994 | Zimmermann | |
| 5,725,530 A | 3/1998 | Popken | |
| 5,826,343 A | 10/1998 | Mollberg, Jr. | |
| 6,178,960 B1 | 1/2001 | Svensson | |
| 6,564,459 B1 | 5/2003 | Steinbrueck et al. | |
| 6,694,623 B1 | 2/2004 | Haughey | |
| 6,782,627 B2 | 8/2004 | Hermes et al. | |
| 7,155,832 B2 | 1/2007 | Warfel et al. | |
| 7,743,513 B1 | 6/2010 | Fisher et al. | |
| 8,398,640 B2 | 3/2013 | Hawkins et al. | |
| 8,498,744 B2 | 7/2013 | Odermatt et al. | |
| 9,339,878 B2 | 5/2016 | Fuchs | |
| 9,367,062 B2 | 6/2016 | Volpert | |
| 9,457,489 B2 | 10/2016 | Fuchs | |
| 9,539,717 B2 | 1/2017 | Fuchs | |
| 9,579,783 B2 | 2/2017 | Wirnitzer et al. | |
| 9,610,698 B2 | 4/2017 | Fuchs | |
| 9,616,512 B1 | 4/2017 | Viola | |
| 9,701,037 B2 | 7/2017 | Zieger et al. | |
| 9,707,677 B2 | 7/2017 | Zieger et al. | |
| 9,724,841 B2 | 8/2017 | Engelfried et al. | |
| 9,744,606 B2 | 8/2017 | Engelfried et al. | |
| 9,744,684 B2 | 8/2017 | Fuchs | |
| 9,744,686 B2 | 8/2017 | Engelfried et al. | |
| 9,789,625 B2 | 10/2017 | Engelfried et al. | |
| 9,789,627 B2 | 10/2017 | Engelfried et al. | |
| 9,844,824 B2 | 12/2017 | Fuchs | |
| 9,937,573 B2 | 4/2018 | Haldar | |
| 9,962,854 B2 | 5/2018 | Hug et al. | |
| 10,052,785 B2 | 8/2018 | Fuchs et al. | |
| 10,160,135 B2 | 12/2018 | Bozic | |
| 10,173,339 B2 | 1/2019 | Fuchs et al. | |
| 10,350,782 B2 | 7/2019 | Engelfried et al. | |
| 10,384,367 B2 | 8/2019 | Engelfried et al. | |
| 10,391,568 B2 | 8/2019 | Fuchs | |
| 10,406,714 B2 | 9/2019 | Duerr et al. | |
| 10,486,326 B2 | 11/2019 | Fuchs | |
| 10,500,656 B2 | 12/2019 | Lutz et al. | |
| 10,639,731 B2 | 5/2020 | Engelfried et al. | |
| 10,695,939 B2 | 6/2020 | Fuchs et al. | |
| 11,192,271 B2 | 12/2021 | Roden et al. | |
| 2003/0045883 A1 | 3/2003 | Chow et al. | |
| 2005/0028375 A1 | 2/2005 | Stones et al. | |
| 2006/0009796 A1 | 1/2006 | Carusillo et al. | |
| 2006/0122616 A1 | 6/2006 | Bennett et al. | |
| 2006/0200161 A1 | 9/2006 | Plaskos et al. | |
| 2006/0229649 A1 | 10/2006 | Levesque et al. | |
| 2007/0123896 A1 | 5/2007 | Wyss et al. | |
| 2008/0033443 A1 | 2/2008 | Sikora et al. | |
| 2008/0140081 A1 | 6/2008 | Heavener et al. | |
| 2011/0005088 A1 | 1/2011 | Pellenc | |
| 2011/0314682 A1 | 12/2011 | Maag et al. | |
| 2012/0279074 A1 | 11/2012 | Ruth | |
| 2013/0228058 A1 | 9/2013 | Gruber et al. | |
| 2014/0059868 A1 | 3/2014 | Engelfried et al. | |
| 2014/0060279 A1 | 3/2014 | Fuchs | |
| 2014/0083884 A1 | 3/2014 | Everett | |
| 2014/0106915 A1 | 4/2014 | Kistler et al. | |
| 2014/0123504 A1 | 5/2014 | Fuchs | |
| 2014/0123827 A1 | 5/2014 | Fuchs et al. | |
| 2015/0122102 A1 | 5/2015 | Engelfried et al. | |
| 2016/0052158 A1 | 2/2016 | Luedtke | |
| 2017/0320227 A1 | 11/2017 | Engelfried et al. | |
| 2018/0162007 A1 | 6/2018 | Engelfried et al. | |
| 2019/0223393 A1 * | 7/2019 | Blevens | A01G 23/083 |
| 2019/0388158 A1 | 12/2019 | Mahfouz | |
| 2020/0001493 A1 | 1/2020 | Engelfried et al. | |
| 2020/0038978 A1 | 2/2020 | Fuchs | |
| 2021/0235626 A1 | 8/2021 | Gerstenberger et al. | |

FOREIGN PATENT DOCUMENTS

| | | |
|---|---|---|
| EP | 2866987 B1 | 4/2020 |
| EP | 2866988 B1 | 5/2020 |
| ES | 1154011 U | 4/2016 |
| GB | 2354481 A | 3/2001 |
| KR | 2020200002598 U | 12/2020 |
| WO | 2014001066 A1 | 1/2014 |

OTHER PUBLICATIONS

Bosch Stories, "Small chain, big impact; NanoBlade: a technology which revolutionizes sawing," Robert Bosch GmbH (https://www.bosch.com/stories/nanoblade-small-chain-big-impact/), 10 pages (undated).
International Search Report and Written Opinion for International Application No. PCT/US2021/043433 dated Dec. 13, 2021.
International Search Report and Written Opinion for International Application No. PCT/US2022/014679, dated Jul. 1, 2022.
International Search Report and Written Opinion for International Application No. PCT/US2022/028792, Dated Aug. 12, 2022.
MAKO TKA Surgical Guide, PN 210469 Rev 00, 64 pages (2016).
Alessi, A., et al., "The Functionality of a Novel Robotic Surgical Assistant for Total Knee Arthroplasty: A Case Series," Case Reports in Orthopedics, vol. 2021, Article ID 6659707, 18 pages (Mar. 17, 2021).
BuildingPoint Central, "Why Use 3D Laser Scanning in Home Building and Renovations," https://buildingpointcentral.com/why-use-3d-laser-scanning-in-home-building-and-renovations/, 11 pages (Sep. 13, 2021).
Cobot Nation, "Cobot Nation Partners with Cognex to Utilize Machine Vision with Collaborative Robots," 3 pages (Aug. 18, 2021).
Halanski, M.A., "How to Avoid Cast Saw Complications," Journal of Pediatric Orthopaedics, 36:S1-S5 (2016).

(56) References Cited

OTHER PUBLICATIONS

Intellijoint Surgical, "Intellijoint Surgical Launches New Smart Navigation Solution for Total Knee Replacements—Intellijoint Knee," 5 pages (Mar. 3, 2020).
Newmarker, C., "CORI Handheld Robotics System Launches with Smith+Nephew Real Intelligence Line," https://www.therobotreport.com/cori-handheld-robotics-system-launched-smithandnephew/, 5 pages (Jul. 14, 2020).
Parratte, S., et al., "Accuracy of a New Robotically Assisted Technique for Total Knee Arthroplasty: A Cadaveric Study," J Arthroplasty, 34 (11), pp. 2799-2803 (2019).
Schwarzkopf, R., "The use of imageless navigation to quantify cutting error in total knee arthroplasty," Knee Surgery & Related Research 33:43, 9 pages (2021).
Stryker Surgical, "The Stryker Precision Oscillating Tip Saw," product brochure, 2 pages (2006).
Weytoll, "Weytoll 4 Inch Electric Drill Modified to Electric Chainsaw Tool Attachment Electric Chainsaws Accessory Practical Modification Tool Set Woodworking Cutting Tool," listing from amazon.com, 14 pages (available from May 30, 2022).
Zimmer Biomet, "ROSA Knee System Surgical Technique V 1.1," 60 pages (2020).

\* cited by examiner

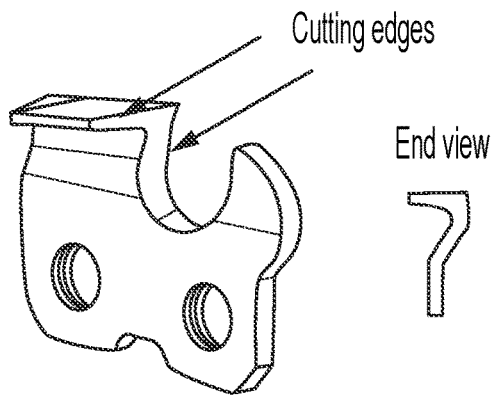
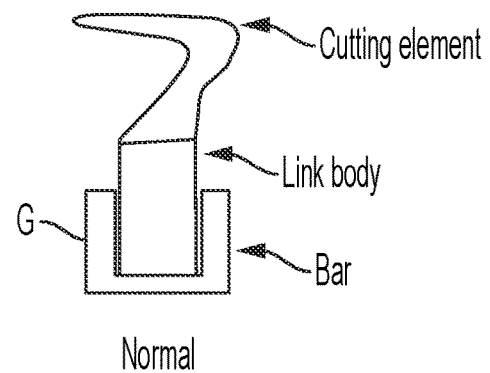
FIG. 11A  FIG. 11B
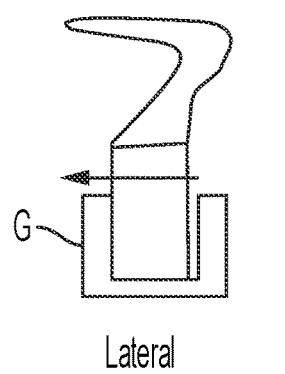
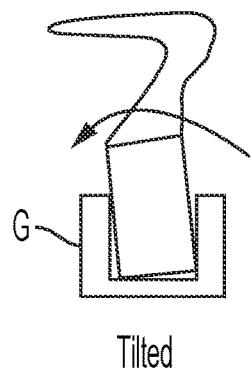
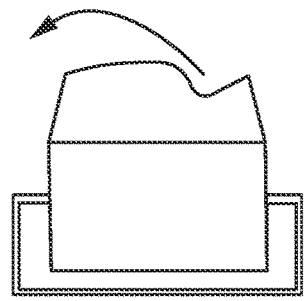
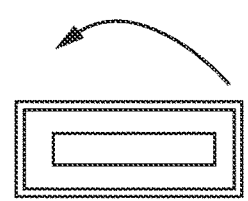
FIG. 11C   FIG. 11D   FIG. 11E   FIG. 11F
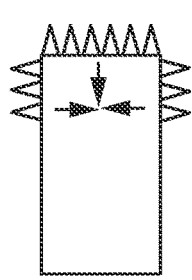
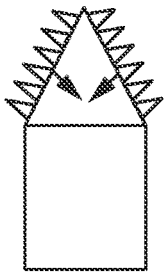
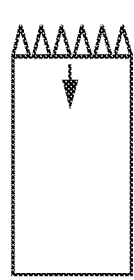
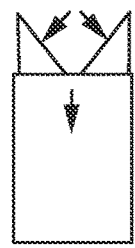
FIG. 12A   FIG. 12B   FIG. 12C   FIG. 12D

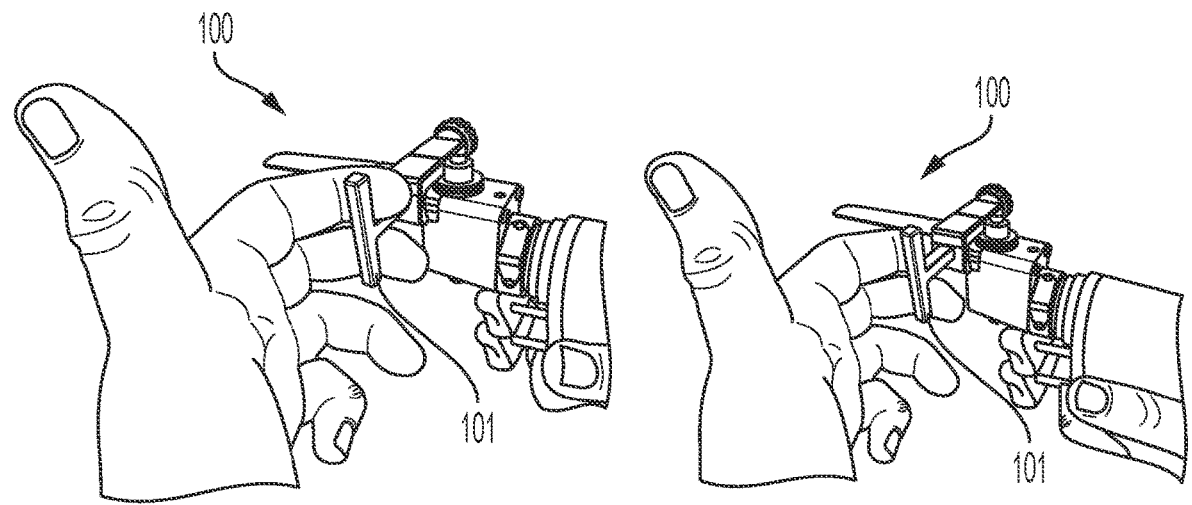
FIG. 15D
FIG. 15E
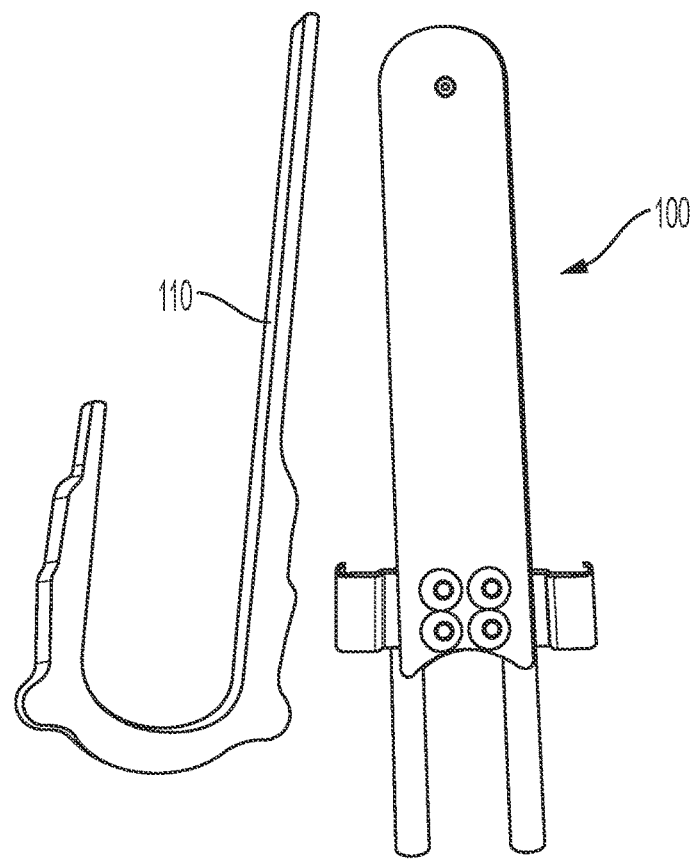
FIG. 16

CHAIN SAWS, COMPONENTS FOR CHAIN SAWS, AND SYSTEMS FOR OPERATING SAWS

CROSS-REFERENCE TO RELATED APPLICATIONS

This application claims priority to U.S. provisional application Ser. No. 63/058,216 filed Jul. 29, 2020, U.S. provisional application Ser. No. 63/085,290 filed Sep. 30, 2020, U.S. provisional application Ser. No. 63/147,033 filed Feb. 8, 2021, U.S. provisional application Ser. No. 63/154,379 filed Feb. 26, 2021, and U.S. provisional application Ser. No. 63/209,540 filed Jun. 11, 2021. The entire contents of these U.S. provisional patent applications are hereby incorporated herein by reference.

TECHNICAL FIELD

The present disclosure is directed to chain saws, components for chain saws, methods of making chain saws and components, and methods of using chain saws and components. The present disclosure is also directed to systems for robotic and automated surgery, particularly orthopedic surgery, such as knee surgery or spinal surgery.

BACKGROUND

Many people suffer from orthopedic conditions in which the cutting of bone or other tissue is required or useful. As an example, many people suffer from serious joint problems that require surgical procedures to implant artificial joints. Every year physicians implant millions of artificial joints in procedures that require the patient's bone to be modified to accept the implant. The most common joint procedure is knee replacement. The modification of bone in knee replacements involves making a series of flat cuts at the ends of the two main adjacent long bones that will be joined by the implant. Ideally these cuts are made precisely complementary to the shape of the implant. A flat surface of healthy bone opposed to the analogous surface of the implant results in the strongest healing of the connection, with less chance of complications or implant failure.

Sawing bone or other tissue during surgical procedures has requirements beyond those in other sawing applications. Specifically, in surgical procedures, the saw must be sterile, the saw bar needs to be easy to control by the surgeon, and vibration and loud sounds need to be minimized. In addition, the saw must perform the cutting in a way that does not generate excessive heat, the procedure must not deposit metal particles or other contaminants in the surgical field, and the procedure must result in cutting hard bone or other tissue while minimizing injury to adjacent soft tissue, among other considerations.

Bone is a living material that contains cells to reform the bone and to fight infection. It is important that after a cut the hard part of bone remains intact and that the bone is not devitalized (the cells killed within the bone). Devitalized bone heals poorly and is less resistant to infection. In an implanted joint, when the bone is devitalized the interface between bone and the implant is impaired, increasing the chances of failure.

One cause of devitalized bone is excessive heat cause by the friction of the cutting device against bone. Without precautions bone temperatures can exceed 200° C. It is important to avoid high temperatures to avoid thermal necrosis, i.e., killing of the cells due to heat, or otherwise damaging or retarding the healing of bone cells due to thermal effects. Bone temperatures can be controlled by shorter cutting times and water irrigation. However, this lengthens the overall procedure time, and the irrigation obscures the cutting field and can be splashed by the vibrations of the cutting device.

The remnants of a bone cut must be removed from the body. Preferably the debris of bone cuts is a mix of powdered bone with body fluid. This slurry should be removed from the cut area. It is undesirable to leave gross pieces of bone behind; if they are deposited in tissue they can act as a nidus for infection.

Bone has variable hardness. Cortical bone, the weight bearing bone tissue on the outside of a long bone, is relatively hard. By contrast, cancellous bone, the bone marrow tissue in the inside of long bones, is relatively soft. Many variations of bone tissue and hardness exist.

The cuts made by a bone saw are ideally flat in the plane of the bar and straight at the cut borders. This is needed to allow optimal healing when two bone surfaces are opposed to each other or when one bone surface is opposed to an implant surface. Surfaces that are not in the same plane, or uneven surfaces, form empty gaps which may take a long time to heal or may never heal. Some saws tend to experience drifting away from the intended plane of the saw bar, called skiving, which is undesirable. Also, some saws have cutting elements that tend to experience a grabbing action that results in unguided movement of the bar, which is also undesirable.

In a surgical procedure, a bone saw is controlled by a surgeon in an operating room environment. Preferably the saw produces minimal vibration so that it can be easily controlled by the surgeon. This is important for multiple reasons. Bones are typically next to important and delicate soft tissue such as blood vessels and nerves, and uncontrolled movement can result in damage to such tissue. Also, uncontrolled movement can result in less desirable cuts.

It is preferable that the saw be thin. In common applications it is desirable when cutting bone to minimize the amount of bone removed. In addition, there are many other orthopedic indications where a small saw is required, an example being surgical implants into vertebrae. Therefore, having a saw design that can be made at sufficiently small sizes to operate as intended is desirable.

In typical bone cutting procedures, the device currently used for cutting bone is a sagittal saw. This saw has a rectangular shape with its cutting edge at one end. The cutting edge moves from side to side through an arc, much like a pendulum. This movement is performed at an extremely high rate, up to 20,000 movements per minute.

There are several disadvantages to a sagittal saw. The sagittal saw produces a large amount of vibration due to the fast motion and high forces used. This makes it difficult for the surgeon to use with precision. The sound of a sagittal saw can be quite loud. In fact, noise-induced hearing loss can be an occupational hazard for operating room personnel. Metal particles can be shaved off the sagittal saw and deposited in the wound. The high speed of the sagittal saw can also result in airborne pathogens, which can be detrimental to the patient, the sterile field, and the medical personnel involved. The high speed of the sagittal saw also produces heat in the bone. This heat can kill the cellular elements within bone, thereby hampering bone healing. To reduce heat, surgeons often limit how long the sagittal saw is continuously used. However, this lengthens the overall time of the procedure. The sagittal saw often deviates from its intended path, thereby making a curved rather than flat bone surface. For these reasons as well as others, the sagittal saw is not ideal.

Chain saws have long been used in applications such as wood cutting; however, until now they have not been successfully deployed for common surgical use. This is due to many technical challenges of the chain saw for the specific requirements of bone or other surgery. U.S. Pat. No. 9,616,512 to Viola discloses a chain saw for cutting bone. The disclosure of U.S. Pat. No. 9,616,512 is hereby incorporated by reference herein in its entirety. Embodiments described herein improve the safety and efficacy of surgical chain saws for cutting bone or other tissue.

Robotic systems for orthopedic surgery are currently known and used. Some embodiments of the present disclosure are directed to robotic or automated systems with one or more advantages over such prior systems.

An example type of system in which robotics is used is an orthopedic stereotaxic instrument for guidance during orthopedic surgery. Such a system typically includes a camera, computer, and tracking arrays. The tracking arrays are placed in a fixed location on the patient, the camera provides images of the tracking arrays in real time to the computer, and the computer converts the image data into location data to track the patient's anatomy. A robot with a surgical tool may be guided based on the location data for the patient's anatomy.

One example of such a robotic system in current use is the Mako Total Knee Arthroplasty ("TKA") System available from Stryker Corporation. The Mako TKA System includes a robot unit having a robotic arm, a camera unit including a stereo 3D camera, and a guidance module. The Mako TKA System further includes tracking arrays, including a femoral tracking array that is attached to the patient's femur and a tibial tracking array that is attached to the patient's tibia, as well as a hand-held probe that can be positioned in various locations by the surgeon. The tracking arrays and the probe have reflective marker discs on them, allowing the camera to track their location. A saw attachment such as a sagittal saw may be attached to the robotic arm.

In use, the robot unit is draped and seated firmly to the floor. The camera unit is on a mast which is also firmly positioned onto the floor. The camera views the tracking arrays on the patient, the system converts the camera image data into location information for anatomical points on the patient, and the system uses this location information to adjust the location of the robotic arm and saw to the desired location of the patient's knee. As the patient's leg moves, the robotic arm readjusts based on the visual feedback from the camera.

Other examples of orthopedic stereotaxic instruments are known. For example, the Rosa Knee System available from Zimmer Biomet is another such instrument. Like the Mako TKA System, the Rosa Knee System uses visualization of anatomical markers to position a robotic arm. The robotic arm of the Rosa Knee System can carry a cut guide for guiding surgical cuts.

There is a need for improvements over such prior systems.

SUMMARY

The present disclosure is directed to improved chain saws, components for chain saws, methods of making chain saws and components, and methods of using chain saws and components. Embodiments of the present disclosure provide improved efficacy and/or safety in cutting bone or other tissue in surgical procedures.

In some embodiments, the saw bar comprises a rail, and the links have grooves such that the links straddle the rail. The rail may have a projection and the grooves of the links may have notches accommodating the projection, whereby the projection prevents dislocation of the links off of the saw bar in a direction away from the path of the chain around the saw bar.

In some embodiments, a chain saw comprises saw bar and a plurality of links arranged in a chain around the saw bar, wherein a first link comprises a hook that engages a recess of a second link, thereby coupling the first link and the second link together and allowing the first and second link to articulate with respect to each other without decoupling as the chain is driven around the saw bar. The links may have one or more cutting teeth oriented such that a cutting action results in forces directed in a substantially vertical direction, i.e., normal to the path of the chain and into the saw bar. The links may have cutting teeth in the shape of cones or pyramids, including oblique pyramids. The links may have cutting teeth aligned along the lateral sides of the links. The peaks of the cutting teeth may be aligned along the lateral sides of the links. The cutting teeth along one lateral side may be staggered with respect to the cutting teeth along the opposite lateral side.

In some embodiments, a hard coating may be applied to the contact surface of the saw bar, i.e., the surface of the saw bar that contacts the links, and/or to the contact surface of the links, i.e., the surface of the links that contacts the saw bar. The hard coating reduces friction and heat generation. The hard coating may also reduce wear and can avoid the need for lubricants, which is beneficial in medical settings in which most lubricants would not be acceptable. The hard coating may be a diamond coating. Other example coatings include nitrides of titanium and titanium alloys as well as other materials, which may be applied by vapor deposition or other processes. A hard coating, such as a diamond coating or other coatings disclosed herein, can also be used to coat the cutting teeth of the links, for similar benefits with respect to reducing friction, heat, and wear.

In some embodiments, the chain saw may include a protective element for protecting the chain saw when passed through a guiding cutting block. The protective element may comprise a first guide post adjacent the chain and spaced from the chain along a first longitudinal side of the saw bar and a second guide post adjacent the chain and spaced from the chain along a second longitudinal side of the saw bar. The guide posts may be wider than the chain. The guide posts may be collapsible. In other embodiments, the protective element may be a collapsible cover.

In some embodiments, a method of orthopedic surgery may comprise operating the chain of a chain saw in a first direction to cut bone and operating the chain of the chain saw in a second direction opposite to the first direction. The cutting teeth may be symmetric or asymmetric, such that the cutting function is the same or different in opposite directions.

In some embodiments, a method of orthopedic surgery may comprise cutting a precise excavated volume in bone with a chain saw and inserting an implant precisely shaped to the excavated volume into the bone.

In some embodiments, systems and method are provided for manufacturing of links for chain saws. In some embodiments, systems and method are provided for low-cost sharpening and/or profiling of cutting teeth for chain saws and other saws.

In some embodiments, a method of manufacturing a link for a chain saw comprises using metal injection molding to mold a link having a first lateral side, a second lateral side, and a plurality of cutting teeth and using grinding (e.g., double disc grinding) to grind the first lateral side and the second lateral side of the link.

In some embodiments, a method of orthopedic surgery may comprise robotically controlling a chain saw to cut bone.

In some embodiments, a robotic system for surgical use comprises an arm comprising a first end and a second end, wherein the first end of the arm is adapted to be connected to a bone of a patient. The second end of the arm is adapted to be connected to one of an instrument, a robotic arm, or a computerized robot unit that includes a robotic arm. The robotic arm may be configured to carry an instrument, such as a bone saw or a guide for a bone saw.

In some embodiments, an automated system for surgical use comprises a chain saw configured to cut bone, a feedback system configured to measure one or more conditions of the chain saw while the chain saw is operating, and a control system configured to receive information from the feedback system and, based on that feedback, to automatically change an input to the chain saw in order to change the operation of the chain saw.

Further examples and features of embodiments of the invention will be evident from the drawings and detailed description.

BRIEF DESCRIPTION OF THE DRAWINGS

The accompanying drawings illustrate examples of devices, components, and methods disclosed herein and, together with the description, serve to explain the principles of the present disclosure.

FIG. 11A shows a prior art chain saw cutting link.

FIG. 11B shows a cross-sectional view of the prior art link of FIG. 11A in a normal position.

FIG. 11C shows a cross-sectional view of the prior art link of FIG. 11A in a laterally displaced position.

FIG. 11D shows a cross-sectional view of the prior art link of FIG. 11A in a tilted position.

FIG. 11E shows a side view of the prior art link of FIG. 11A.

FIG. 11F shows a top view of the prior art link of FIG. 11A.

FIG. 12A shows an example arrangement of cutting elements on three sides of a link.

FIG. 12B shows an example arrangement of cutting elements on two sloped surfaces of a link.

FIG. 12C shows an example arrangement of cutting elements on a top surface a link.

FIG. 12D shows an example arrangement of cutting elements on a top surface a link, with one row of cutting elements along one lateral side of the link and another row of cutting elements along the other lateral side of the link.

FIG. 15D shows the chain saw with surgical handle of FIG. 15A being moved in a first direction.

FIG. 15E shows the chain saw with surgical handle of FIG. 15A being moved in a second direction.

FIG. 16 shows a guard that can be attached to a chain saw.

Figure 1:
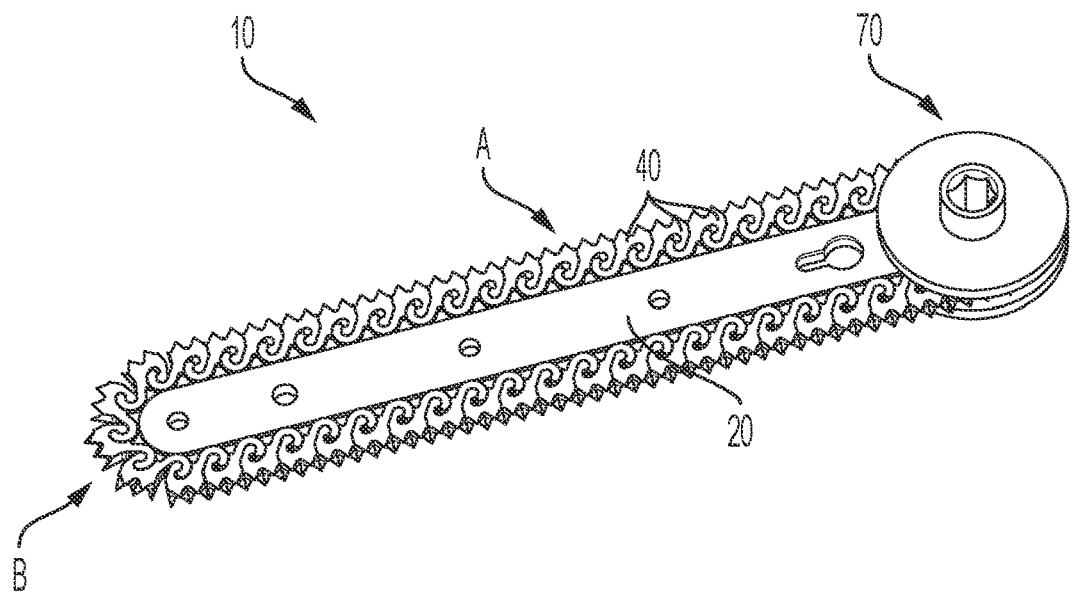
FIG. 1 shows an example embodiment of a chain saw cartridge in accordance with the disclosure.

The accompanying drawings may be better understood by reference to the following detailed description.

DETAILED DESCRIPTION

For the purposes of promoting an understanding of the principles of the disclosure, reference will now be made to the examples illustrated in the drawings, and specific language will be used to describe those and other examples. It will nevertheless be understood that no limitation of the scope of the claims is intended by the examples shown in the drawings or described herein. Any alterations and further modifications to the illustrated or described systems, devices, components, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure.

The designations "first" and "second" as used herein are not meant to indicate or imply any particular positioning or other characteristic. Rather, when the designations "first" and "second" are used herein, they are used only to distinguish one component or part from another. The terms "attached," "connected," "coupled," and the like mean attachment, connection, coupling, etc., of one part to another either directly or indirectly through one or more other parts, unless direct or indirect attachment, connection, coupling, etc., is specified. The term "user" refers to one or more persons using the devices, systems, and/or methods described herein, such as one or more surgeons, physicians, operators, or other persons using the devices, systems, and/or methods.

FIG. 1 shows a first example embodiment of a chain saw cartridge 10 suitable for bone or other tissue cutting in surgical procedures, such as knee surgery, vertebral surgery, and other potential bone or tissue cutting applications. The chain saw cartridge 10 in FIG. 1 comprises a saw bar 20, a plurality of links 40 assembled together in a cutting chain around the bar 20, and a drive cog assembly 70.

Figure 2:
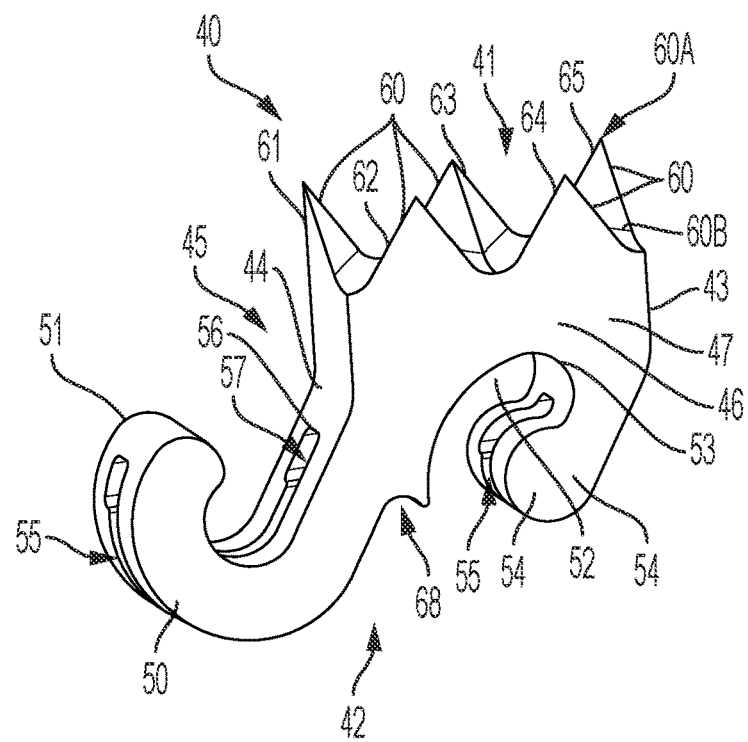
FIG. 2 shows a single link for a cutting chain of a chain saw such as the cutting chain of the chain saw cartridge in FIG. 1.

FIG. 2 shows a single link 40 for a cutting chain of a chain saw such as the cutting chain of chain saw cartridge 10 in FIG. 1. The link 40 comprises a top or cutting side 41, a bottom or bar side 42, a first adjacent link side 43, a second adjacent link side 44, a first lateral side 45, and a second lateral side 46.

The link 40 has a hook 50 and a recess 52. The link 40 has a rounded feature or projection 54 that defines one side of the recess 52. In this example embodiment, the hook 50 extends outward from the second adjacent link side 44 and upward from the bottom side 42, and the rounded projection 54 extends downward from the top side 41 and inward from the first adjacent link side 43. The recess 52 extends upward from the bottom side 42 and is shaped to receive a hook 50 of an adjacent link 40.

As shown in FIG. 1, a plurality of links 40 can be connected together in a chain to move along a predetermined path around the bar 20. The recess 52 of one link receives the hook 50 of an adjacent link, whereby the hook 50 fits into the recess 52. The hook 50 of one link thereby interlocks with the rounded projection 54 of an adjacent link. When two adjacent links are in an aligned or non-articulated configuration with one another, such as along a straight part A of the bar 20, the distance between the tip 51 of the hook 50 and the end 53 of the recess 52 leaves a clearance, allowing for articulation. When two adjacent links are in an articulated configuration along a convex path with one another, such as along a convexly curved part B of the bar 20, the articulation causes the hook 50 to engage further into the recess 52, and distance between the tip 51 of the hook 50 and the end 53 of the recess 52 is smaller than along the straight part A. In some embodiments, at the full extent of articulation, i.e., the maximum degree of pivot between adjacent links, the tip 51 of the hook 50 is at its closest point to, and in some embodiments may touch, the end 53 of the recess 52.

The configuration of the links 40 with the hooks 50 and corresponding recesses 52 allows the links 40 to pivot with respect to each other and to remain connected to each other even as they pivot away from each other along a convexly curved path. The links 40 remain connected, avoiding longitudinal disarticulation, without the need for separate connecting elements such as rivets, pins, or other connectors. Thus, the width of the chain is as thin as the width of the cutting links 40, allowing a thin chain, for a thin kerf.

As shown in FIG. 2, the bottom side 42 of the link 40 has a drive cog engagement recess 68. The drive cog engagement recess 68 is for engagement by a drive cog 72, as described in more detail below.

At the top or cutting side 41, the link 40 has a plurality of cutting teeth 60. In the illustrated embodiment, each cutting tooth 60 is in the shape of a pyramid, tapering from a relatively wide base 60B to a sharp or relatively sharp peak or apex 60A. The illustrated teeth are arranged in two parallel rows, each running along a lateral side of the top side 41 of the link 40. Teeth 61, 63, and 65 are arranged along a first lateral side, and teeth 62 and 64 are arranged along a second lateral side.

Figure 3:
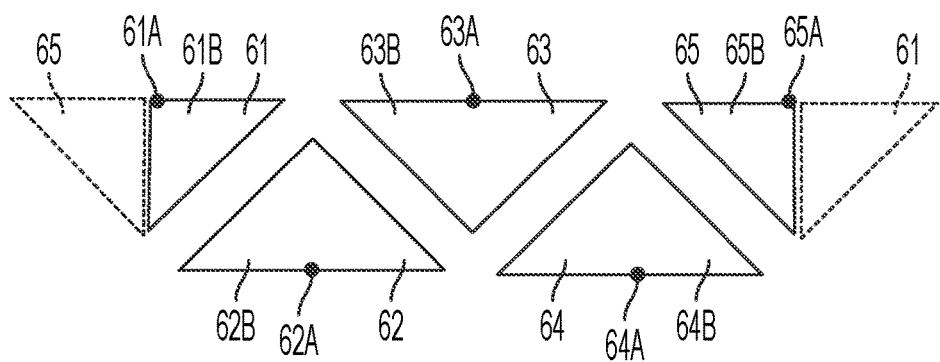
FIG. 3 shows a schematic view of a layout of cutting teeth of a link.

FIG. 3 shows a schematic view of the layout of the cutting teeth 60 of a link 40, showing in solid lines the bases 61B, 62B, 63B, 64B, and 65B of the teeth 61, 62, 63, 64, and 65, respectively. The bases 62B, 63B, 64B of teeth 62, 63, and 64 are triangular and have a first size. The bases 61B and 65B of teeth 61 and 65 are triangular and have a second size that is about half (a range that includes half and nearly half) of the first size. Each of the teeth 61, 62, 63, 64, and 65 is in the shape of an oblique pyramid, with the peak or apex of the pyramid located generally above the points labeled 61A, 62A, 63A, 64A, and 65A, respectively. One side of each pyramid is approximately coplanar or flush with a lateral side of the link 40. That is, each of teeth 61, 63, and 65 has a side that is approximately coplanar with a first lateral side 45 of the link 40, and each of teeth 62 and 64 has a side that is approximately coplanar with a second lateral side 46 of the link 40. In the illustrated embodiment, the peaks of the pyramidal teeth 61, 63, and 65, located generally above the points labeled 61A, 63A, and 65A, respectively, are aligned with the first lateral side 45 of the link 40, and the peaks of the pyramidal teeth 62 and 64, located generally above the points labeled 62A and 64A, respectively, are aligned with the second lateral side 46 of the link 40.

When the link 40 is arranged in a chain with similar links 40, the tooth 61 is adjacent a tooth 65, shown in dotted line, of an adjacent link, and together the adjacent teeth 61, 65 form a tooth profile similar to that of tooth 63. Similarly, when the link 40 is arranged in a chain with similar links 40, the tooth 65 is adjacent a tooth 61, shown in dotted line, of an adjacent link, and together the adjacent teeth 65, 61 form a tooth profile similar to that of tooth 63. In other words, a tooth 61 and an adjacent tooth 65 together form a tooth similar in size and shape to a tooth 63. Thus, when arranged in a chain of links, the chain has two rows of teeth, with teeth 62 and 64 alternating along one lateral side 46, and teeth 63 and 61/65 alternating along the other lateral side 45.

One result of this configuration is that the peaks of the teeth are at either side of the cutting surface with a valley in between. The cutting teeth on opposing sides are staggered such that a peak on one side lines up with a valley between peaks on the opposite side. This reduces the time between cutting impacts, thereby minimizing vibration, while allowing room for removal of bone debris. The shape and arrangement of the cutting teeth also promotes centering of the chain as it cuts. That is, the geometry and arrangement of the cutting teeth leads to self-centering of the links.

The links 40 can have approximately the same width as the saw bar. In such as case, with an arrangement with some pyramidal teeth having sides flush with a first lateral side 45 of the link 40 and other pyramidal teeth having sides flush with a second lateral side 46 of the link 40, the lateral side surfaces of the links (including the teeth) and the bar are continuous and relatively smooth. This aids in making bone cuts with a smooth surface.

The cutting width of the links should be equal to or greater than the width of the bar so that the saw does not bind up. For a chain saw to pass through bone the width of the cut made by the chain must be equal to or greater than the width of the bar. If the bar is wider than the cut it will extend past the cut and will be bound by bone. In some embodiments, such as the example illustrated in FIGS. 2 and 3, the pyramids or cutting elements are at the sides of the links and do not extend laterally beyond the width of the saw bar. In other examples, the pyramids or cutting elements may extend laterally beyond the sides of the links and/or laterally beyond the width of the saw bar.

The cutting teeth may have other shapes and arrangements. The teeth may be shaped as other types of cones, with a pyramidal shape being one example of a cone. A pyramid is a cone with a polygonal base. In the illustrated example, the base of the cone or pyramid is triangular, but other shaped bases may be used, having 4, 5, 6, 7, 8, or more sides. The polygons may have any suitable angle between sides. For example, if triangular bases are used, the triangles may have angles that are acute, 90 degrees, or obtuse. Example triangles have angles of 90 degrees, 45 degrees, and 45 degrees at their corners, or 60 degrees at each corner, or other suitable angle arrangements. Other shapes that the teeth may have include cones with circular, elliptical, or irregular bases. The cones may be right cones or oblique cones. For example, teeth shaped as pyramids may be right pyramids or oblique pyramids. Any edges, apices, or corners of the teeth may be sharp or rounded. The apices may be oriented vertically, or they may be tilted or curved inwardly and/or outwardly. Other shapes that the teeth may have include a concave shape with a cutting edge (like a spoon with a sharp edge) designed to scoop out material. For example, such a design may be used for scooping out volumes of soft tissue, such as when excavating cartilaginous discs between vertebrae. A single link or single chain may have a mix of different sizes, heights, and shapes of cutting teeth, including any of the teeth described above.

The configuration of the cutting teeth as described, for example as shown in FIGS. 2 and 3, orients cutting edges of the teeth toward the bone or other tissue to be cut so that the cutting teeth act as cutting blades that facilitate slicing the bone or tissue. This slicing function is in contrast to the chipping operation of conventional chisel-shaped teeth. Moreover, the arrangement of the cutting teeth with surfaces substantially coplanar with the lateral sides of the links facilitates cuts that have relatively flat and relatively smooth sides. In addition, the configuration of cutting teeth helps prevent clogging by fibrous tissue.

Arranging cutting teeth along lateral sides of the links with a valley in between gives room for removal of bone debris or other debris in the valley between the cutting teeth. The valley can also be used to advance fluids such as sterile saline or other fluids such as those used for cooling or cleansing. The valley also provides a channel for advancing drugs, such as drugs that curb bleeding, prevent infections, or prevent other negative cellular responses. The valley can also be used to advance nonliquid or slurry types of product to facilitate supply in very small areas or in high volumes, such as human growth hormones, calcium, bone substitutes, collagen, etc. Movement of the chain can also act as a conveyor in delivery of substances. Chain saws as described herein with a valley or channel between cutting teeth can also be used for collecting or harvesting bone, for example to collect or harvest bone from the pelvic region in the iliac crest to be used as an autograph material for the patient, generally used for spinal surgery. The bone is harvested by the cutting teeth and carried out of the patient via the valley between the cutting teeth.

In some embodiments, it may be desirable to have one or more cutting elements in the center of the link, between the lateral rows of cutting elements along the sides. This may be desirable in order to cut between the lateral rows. Thus, in some embodiments, one or more links may have one or more center cutting elements, such as one or more chisel-shaped teeth or squared-off teeth. Such a cutting element or cutting elements do not need to be on every link. For example, half or a few or even only one link in a chain may have such a cutting element or cutting elements.

Figure 4A:
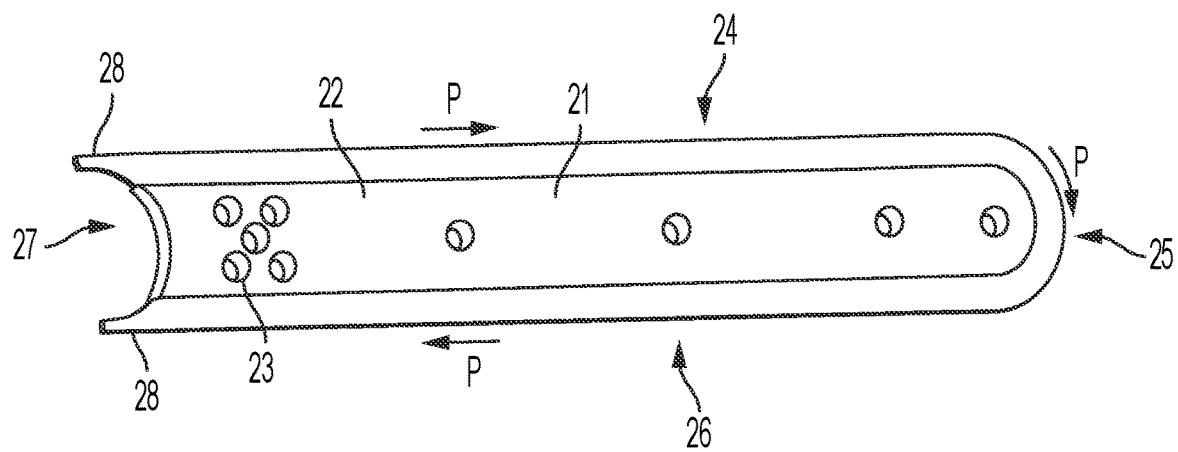
FIG. 4A shows an example embodiment of a saw bar that may be used in a chain saw in accordance with the disclosure.

FIG. 4A shows a saw bar 21 that may be used in the chain saw cartridge 10. Saw bar 20 of FIG. 1 and saw bar 21 of FIG. 4A are similar except for having different holes 23 for fixing the bar 21 to the suspension system that attaches to the driving head of the chain saw. The saw bars 20, 21 are generally planar, with a main body 22 that contributes the primary strength and stability of the bar and allows the links to transmit a normal load with respect to the downward pressure of cutting, i.e., a load that is directed normal to the chain path and toward the saw bar. The bar has two sides 24, 26 in the longitudinal direction and a distal end 25 that in the embodiment of FIG. 4A is curved or semicircular. The bar has a recess at the proximal end 27, for accommodating a drive cog. The sides 24, 26 have extensions 28 that facilitate transfer of the continuous link chain from the bar to the drive cog and from the drive cog to the bar. The first longitudinal side 24, the second longitudinal side 26, and the distal end 25 define at least part of a chain path P around the saw bar 21.

Figure 4B:
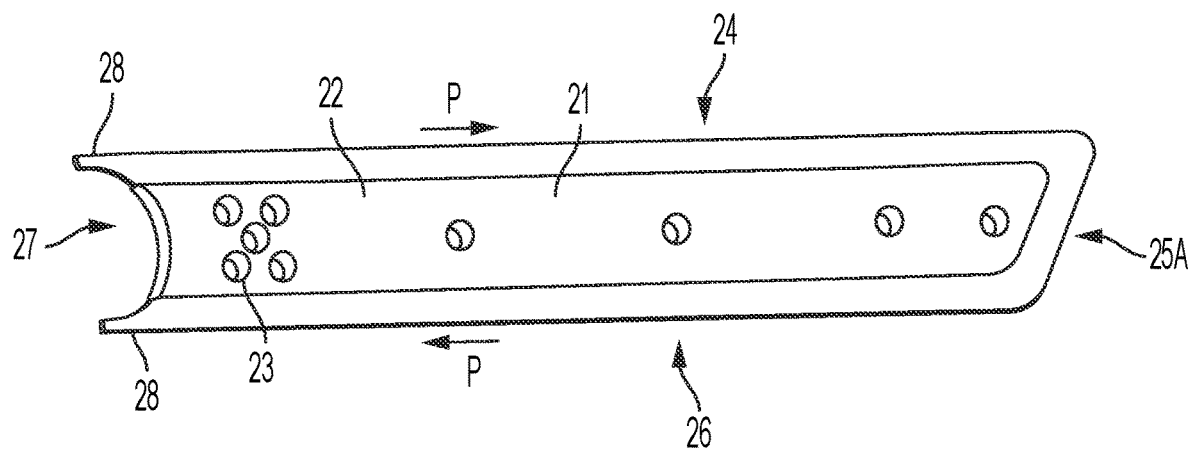
FIG. 4B shows an alternative example embodiment of a saw bar that may be used in a chain saw in accordance with the disclosure.

The bar 20, 21 could have various other configurations. For example, the distal end 25 can be symmetrical and semicircular as shown in FIG. 4A, or it can have other shapes. In one alternative, as shown in FIG. 4B, the distal end 25A can be asymmetrical, presenting a sloped face with rounded ends that projects more on one side of the saw than the other. The sloped face may be relatively straight and angled with respect to a longitudinal axis of the saw bar such that one longitudinal side of the saw is longer than the other, and the sloped face may have rounded ends where it transitions to the longitudinal sides. Such a distal tip could be desirable in some types of surgery to resist the lateral forces produced by the moving chain approaching a piece of bone straight on.

Figure 5A:
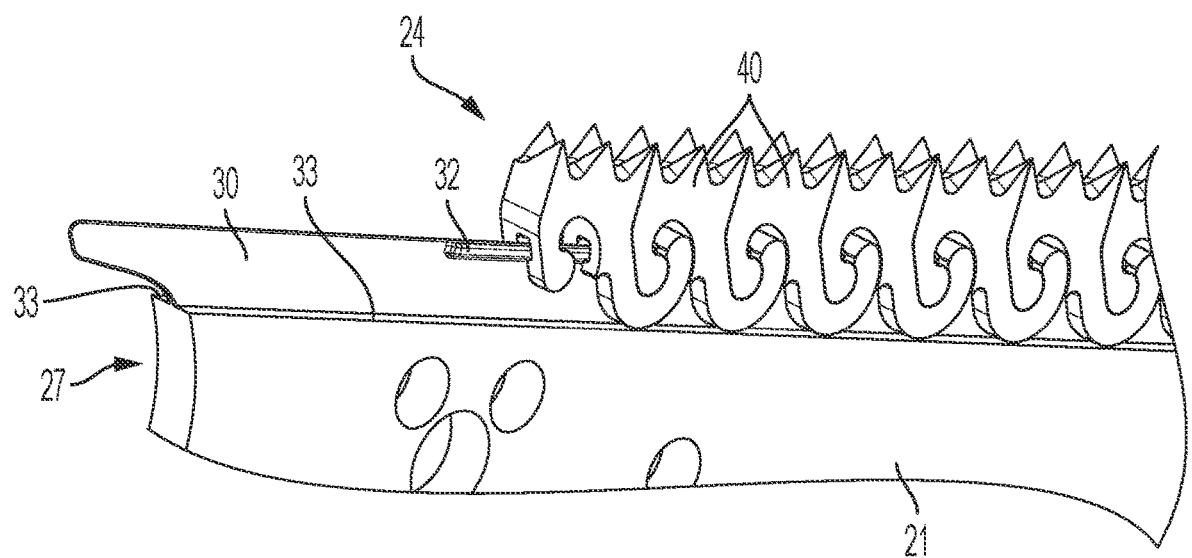
FIG. 5A shows an enlarged view of the saw bar of FIG. 4A, with a chain of links assembled on the bar, in a partial cut-away view.
Figure 5B:
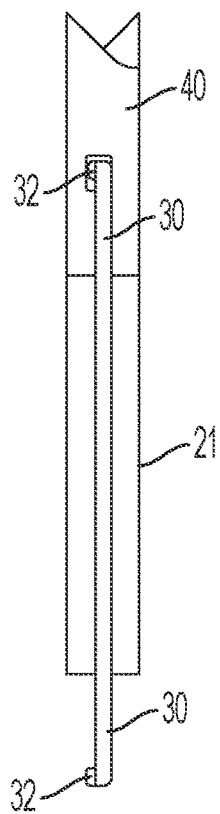
FIG. 5B shows an enlarged end view of the saw bar of FIG. 4A at the distal end of the bar, with a single link shown.
Figure 5C:
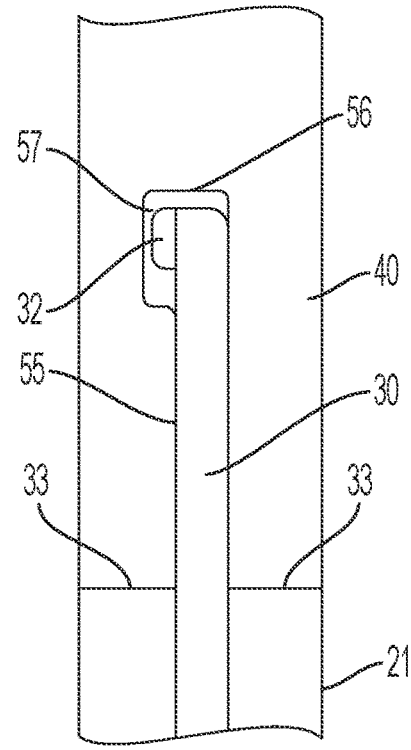
FIG. 5C is an enlarged view of a portion of FIG. 5B.

FIG. 5A shows an enlarged view of a first side 24 of the bar 21 at the proximal end 27 of the bar 21, with part of a chain of links 40 assembled on the bar 21, shown in a partial cut-away view. FIG. 5B shows an enlarged end view of the bar 21 at the distal end 25 of the bar 21, with a single link 40 shown for illustration purposes. FIG. 5C is an enlarged view of a portion of FIG. 5B.

As shown in FIGS. 5A, 5B, and 5C, the bar 21 has a rail 30 extending from the main body 22 of the bar 21. The rail 30 extends, in whole or in part, along the sides 24, 26 and the distal end 25 of the bar 21. The rail 30 acts as a monorail along which the links 40 of the chain travel. The rail 30 generally extends in a direction away from the main body 22 of the bar 21. The rail 30 includes a projection 32 that extends laterally beyond one or both sides of the rail 30. The projection 32 acts as a link lock or retention element that prevents the links 40 from coming off of the rail 30 in a direction away from the bar, i.e., in a direction away from the bar generally perpendicular to the direction of travel of the chain.

The links 40 have grooves in them so that the links 40 fit over and straddle the monorail 30. As shown in FIG. 2, the illustrated link 40 has a groove 55 that extends from the bottom side 42 of the link 40 upward part of the way to the top side 41 of the link 40. The top end of the groove 55 is labeled as top end 56. The groove 55 runs parallel to and is located between the first lateral side 45 and the second lateral side 46 of the link 40. The groove 55 extends the longitudinal length of the link 40, from the first adjacent link side 43 through the rounded projection 54 through the link body 47 and the second adjacent link side 44 and through the hook 50. The groove 55 includes a notch 57 that extends laterally beyond one or both sides of the groove 55. The notch 57 is shaped to accommodate the projection 32 of the rail 30.

As shown in FIG. 5C, the groove 55 and notch 57 of a link 40 accommodate the rail 30 and projection 32 of the bar 20, 21 to allow the links 40 to travel around the bar 20, 21 while preventing the links 40 from coming off of the rail 30 in a direction away from the bar 20, 21. In the illustrated example, when the links 40 are assembled on the rail 30, a clearance space is present between the top of the rail 30 and the top end 56 of the groove 55. In addition, in this example, a clearance space is present between the bottom of the notch 57 and the bottom of the projection 32. This allows some small movement or play of the links 40 in a direction away from the bar 20, 21 perpendicular to the direction of travel of the chain around the bar 20, 21. Also, in this example, the width of the groove 55 is slightly wider than the width of the rail 30. This allows some small movement or play of the links 40 in a lateral direction with respect to the bar 20, 21, while the rail 30 and groove 55 prevent any unwanted excessive movement of the links 40 in a lateral direction with respect to the bar 20, 21.

The clearance between the rail 30 and the groove 55 also results in the vertical load from the links 40, i.e., the load in a direction normal to the chain path directed into the saw bar, being taken up by the main body of the saw bar as opposed to the rail 30 itself. Vertical forces from the cutting pyramids of the links 40 are transmitted from the links 40 directly to the skids or ledges 33 of the saw bar on either side of the rail 30. The rail 30 itself is not loaded by these vertical forces. This arrangement tends to press the links 40 into place, while the rail 30 provides resistance to lateral movement or rocking motions of the links.

In other words, the ledges 33 are where the normal downward load from the links is primarily carried. The tangent sections at the bottom of the link 40, i.e., the tangent sections at the bottom of the hook 50 and the projection 54, contact the ledges 33 on either side of the rail 30. Because of the groove 56, the link 40 straddles the rail 30, with one side of the link 40 contacting the ledge 33 on one side of the rail 30 and the other side of the link 40 contacting the ledge 33 on the other side of the rail 30. The separation of the right link side to ledge contact and left link side to ledge contact provides inherent stability and planar control of the link with respect to the bar. The ledges 33 bear the downward forces from the links 40, resulting in stabilizing the links 40 and maintaining the links 40 in the same plane as the plane of the bar. This helps assure that the lateral sides of the links 40 remain substantially coplanar with the sides of the bar 20, 21.

The projection 32 and notch 57 may take any suitable shapes for allowing the links 40 to travel around the bar 20, 21 while preventing the links 40 from coming off of the rail 30 in a direction away from the bar 20, 21. For example, the projection 32 may have a cross-sectional shape of a circle, oval, polygon, or irregular shape, and the notch 57 may have any suitable shape for accommodating the projection 32 while keeping the links 40 on the rail 30. The projection may be symmetrical or asymmetrical and may extend from one or both sides, and the notch similarly may be symmetrical or asymmetrical and may extend from one or both sides.

In an alternative embodiment, the rail 30 has a notch (like the notch 57) and the groove 56 of the links 40 have projections (like the projection 57) that fit in the notch. This alternative arrangement (switching the locations of the projection and notch) provides a similar link lock or retention element as described above, preventing the links 40 from coming off of the rail 30 in a direction away from the bar. The link locking feature on the saw bar, i.e., the projection or notch, may extend around the entire saw bar or only part(s) of the saw bar.

To mount the chain on the saw bar, the links may be coupled to each other. Then the end of the chain can be placed over the end of the rail 30, with the notch 57 of the end link 40 placed around the projection 32. Then the chain can be guided onto the rail 30 in the direction of the rail 30 and guided along the rail 30 around the saw bar 20, 21. The chain also fits around the drive cog 72 and can be tensioned.

Figure 6A:
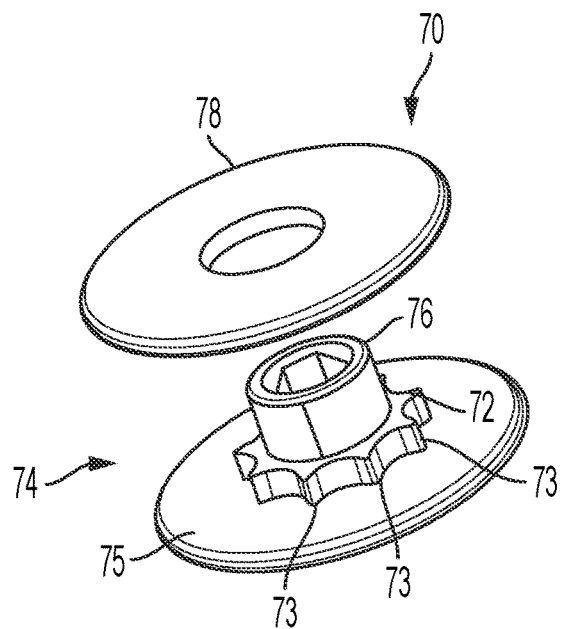
FIG. 6A shows an exploded view of a drive cog assembly of a chain saw in accordance with the disclosure.
Figure 6B:
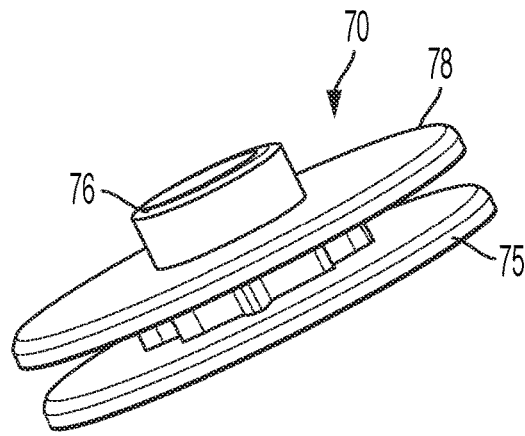
FIG. 6B shows a side perspective view of the drive cog assembly of FIG. 6A.
Figure 6C:
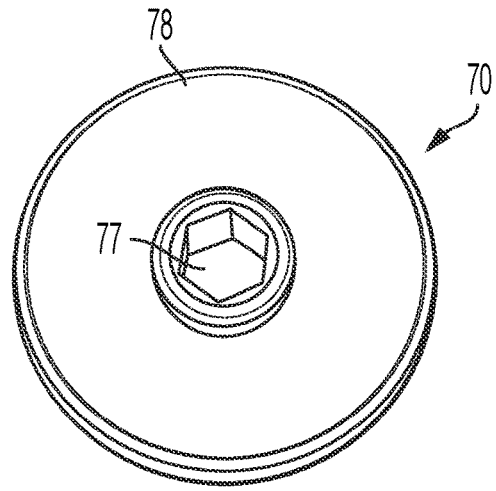
FIG. 6C shows a top perspective view of the drive cog assembly of FIG. 6A.

FIG. 6A shows an exploded view of the drive cog assembly 70 of a chain saw in accordance with the disclosure. FIG. 6B shows a side perspective view of the drive cog assembly 70. FIG. 6C shows a top perspective view of the drive cog assembly 70.

The drive cog assembly 70 includes a drive cog 72 with a series of drive cog teeth 73 around the perimeter of the drive cog 72. In operation, the chain of links 40 goes around the bar 20, 21 and around the drive cog 72, as shown in FIG. 1. The drive cog teeth 73 engage the drive cog engagement recesses 68 of the links 40. When the chain saw cartridge 10 is attached to a driving mechanism, the driving mechanism causes the drive cog 72 to rotate, thereby causing the chain of links to move around the bar 20, 21 due to the engagement between the drive cog 72 and the links 40.

In the illustrated example, the drive cog assembly 70 includes a main body 74 having a plate or disk 75 and a central post 76. The central post 76 has a shaped hole or recess 77, having a hexagonal or other shaped cross-section for receiving a driving element. For example, the hole or recess 77 can mate with the gearing of a power adapter. The drive cog assembly 70 further includes the drive cog 72 and a cap 78. The drive cog 72 could be manufactured as one unit with the plate 75 or as a separate piece that is assembled to the plate 75. For example, the drive cog 72 may have a central hole sized to accommodate the post 76 so that the drive cog 72 fits over the post 76, for example in a press fit, to be placed against the plate 75. The cap 78 may also have a central hole sized to accommodate the post 76 so that the cap fits over the post 76, for example in a press fit, to be placed against the drive cog 72. Two or more of the parts of the drive cog assembly 70 may be affixed together by laser welding or another suitable process.

In an example of assembling the chain saw cartridge 10, the chain of links 40 may be assembled around the bar 20, 21 and the drive cog 72. The components of the chain saw cartridge 10 may be locked together by joining the cap 78 to the remainder of the drive cog assembly 70. Once the chain saw cartridge 10 is assembled, the components of the chain saw cartridge 10 will not disassociate due to its interlocking and overlapping assembly and construction. Thus, the chain saw cartridge 10 cannot come apart naturally on its own. The chain saw cartridge 10 may be a disposable item that could be packaged sterile and sold separately from the power equipment used to drive the chain of the chain saw. For example, the chain saw cartridge 10 may be supplied as a unified assembly for attachment to a chain saw driving head, such as the chain saw driving head 12 in FIG. 10, as described in further detail below.

The chain saw may include a mechanism for determining the position of the chain around the bar. For example, the shaped hole or recess 77 for receiving the driving element may be a single position key, such that the driving element fits in only one position. Thus, the position of the driving element with respect to the drive cog 72 and thus the position of the chain of links 40 can be known. Additionally or alternatively, the drive cog assembly or other part of the chain saw may include a position indicator, such as a mechanical, magnetic, or optical encoder or Hall effect mechanism, that gives feedback to the drive unit. With such feedback, the operator or computer operated control gets information regarding the rotation of the travel and/or positioning of the teeth. In an example embodiment, a chain saw may have some section of the plurality of teeth designed for a specific purpose. For example, a chain saw may have a section with very small nonaggressive cutting features as compared to the remainder of the chain. By knowing the position of the chain, the operator or computer control can selectively position the sections of teeth as desired. For example, the less aggressive cutting teeth can be positioned distally when plunging near sensitive soft tissue or other physiology such as nerves or arteries, and the chain can be operated in an oscillatory motion so that the less aggressive teeth remain positioned distally. The cutting can be performed with these less aggressive teeth as they slowly break through the bone. After that sensitive section is addressed, the chain can be operated to rotate continually and expose the bone to the more aggressive tooth profile.

One potential issue with ordinary chain saws is friction, such as between the chain and saw bar. Friction also produces heat, which can be disadvantageous in surgical settings. With certain prior art saws, to reduce heat the bar must be irrigated, e.g., with saline, or the saw may be used only for short periods.

In accordance with some embodiments of the invention, to reduce friction a very hard coating may be applied to the surface of the either the bar 20, 21 or links 40 where they contact each other. One non-limiting example is a diamond coating. A hard coating such as a diamond coating greatly decreases the friction between the bar and link surfaces. This minimized friction decreases the heat generation of sawing. This allows the saw to be used for longer continuous periods, thereby shortening the overall time of the procedure. The hard coating can also reduce wear. In addition, with a hard coating, embodiments of chain saws disclosed herein may be operated without the need for any external lubricants to facilitate the cooling or lubrication of the assembly. External lubricants can be disadvantageous in that they can cause contamination. In addition, there is decreased need, or no need, for irrigating the bar. Irrigation can be troublesome as it may obscure the view of the cutting and may splatter irrigation fluid outside the surgical field.

Figure 7A:
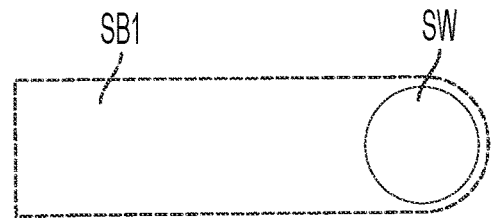
FIG. 7A shows an example of a saw bar with a sprocket wheel.

An unexpected finding was that with such a coating the friction can be decreased to the extent that a sprocket wheel is not required. Without such a coating, the course of the chain around the curved distal end of the saw generates a large amount of friction. To eliminate this friction a sprocket wheel may be placed at the distal end. FIG. 7A shows an example of a saw bar SB1 with a sprocket wheel SW. This sprocket wheel SW can rotate at the speed of the chain around the saw bar and practically eliminates the friction caused by the acute turn at the end of the saw bar.

Figure 7B:
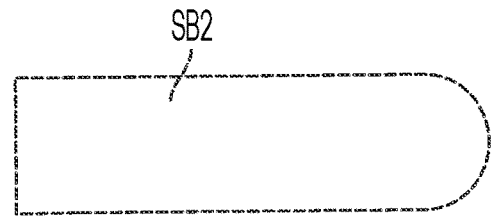
FIG. 7B shows an example of a saw bar with a hard coating and without a sprocket wheel.

FIG. 7B shows an example of a saw bar SB2 with a hard or friction-minimizing coating such as a diamond coating on the bar, which eliminates the need for a sprocket wheel SW. The elimination of a sprocket wheel greatly simplifies the saw. It makes the saw bar easier and cheaper to manufacture while making it stronger, and it greatly aids in producing miniature versions of the device.

As mentioned above, the hard coating that may be applied to the contact surface(s) of the saw bar and/or links may be a diamond coating. Other example coatings include nitrides of titanium and titanium alloys as well as other materials, which may be applied by vapor deposition or other processes. A hard coating, such as a diamond coating or other coatings disclosed herein, can be used to coat all or any portion of the saw bar and/or of the links. For example, a hard coating as disclosed herein can be used to coat the cutting teeth of the links, which can reduce friction, heat, and wear. The entirety of the links may be coated with a hard coating, which results in coating both the surface of the links that contacts the saw bar and the cutting teeth.

Figure 8:
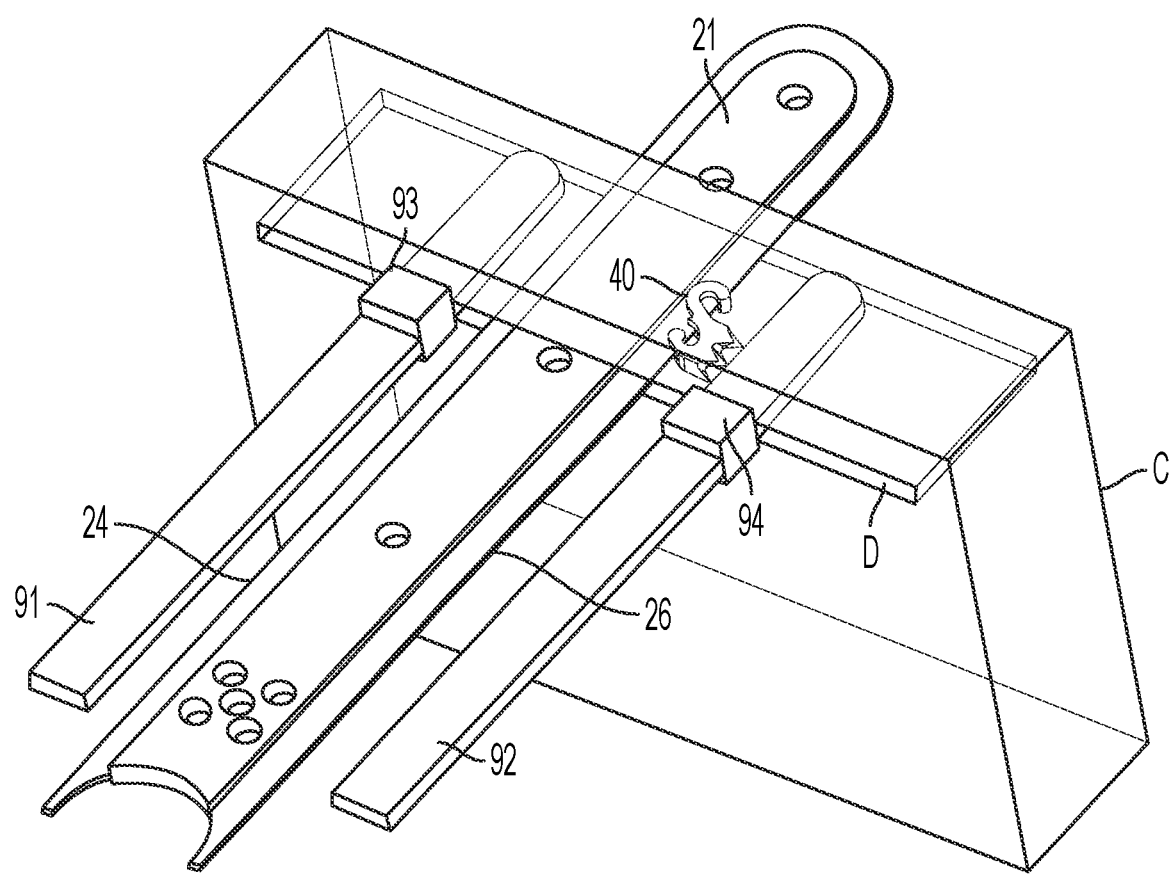
FIG. 8 shows an example embodiment of a chain saw with guide posts in accordance with the disclosure.

FIG. 8 shows an additional feature that can be incorporated as part of a chain saw or chain saw system in accordance with the disclosure. Certain procedures such as knee replacement surgery or other orthopedic procedures can use cutting blocks such as the cutting block C shown in FIG. 8. The cutting block C has a window D through which a saw may be guided. In use, the cutting block C may be secured to the patient, such as to bone, so that the saw is guided to make a cut in a desired location. The cutting block C fixes the location of the cut and helps prevent unwanted movement of the saw.

Because the chain of the chain saw must pass through the window D of the cutting block C, there is a danger of the chain (one link 40 shown in FIG. 8) contacting the right or left inner sides of the cutting block window D, which could cause damage to and debris from both the links/chain and the cutting block C. In addition, because the chain of the chain saw must pass through the window D of the cutting block C, the width of the window D should be larger than the width of the chain. However, this could lead to unwanted movement of the chain saw, as well as the potential for the links/chain to contact the top or bottom surfaces of the cutting block window D, causing similar issues of damage and debris.

In accordance with the embodiment of FIG. 8, the chain saw includes guide posts 91, 92 that extend forward on either side of the saw bar 21, spaced from the chain on the longitudinal sides 24, 26 (sometimes referred to as the top and bottom) of the saw bar 21 as shown. These stabilizing guide posts 91, 92 are rigidly affixed at their proximal ends (not shown) to the same mechanism as the chain saw cartridge 10, such as the driving head of the chain saw, so that the guide posts 91, 92 are at a fixed position with respect to the saw bar 21 and move together with the saw bar 21 as a rigid assembly. That is, the guide posts 91, 92 are held at a fixed distance from the saw bar 21 on either side of the saw bar 21.

Because the guide posts 91, 92 are on either side of the saw bar 21, they prevent the chain from contacting the right or left inner sides of the cutting block window D. In addition, the guide posts 91, 92 are slightly thicker than the chain saw. In this way the guide posts 91, 92 are in contact with the top and bottom walls of the cutting block window D. This prevents unwanted angular motion of the saw bar 21 as well as maintains the saw at a proper position spaced from the top and bottom surfaces of the window D. Thus, contact between the moving chain and the window surfaces is avoided.

In order to avoid having the guide posts 91, 92 extend significantly beyond the distal side of the window D, each of the guide posts 91, 92 may be collapsible along its longitudinal axis. Specifically, the guide posts 91, 92 may have telescoping parts, with stops 93, 94 on the distal parts. When these stops 93, 94 contact the entry into the window D, they cannot go further. As the saw bar 21 is continued to be advanced through the window D, the distal parts of the guide posts 91, 92 are prevented from advancing due to the stops 93, 94, and the guide posts 91, 92 shorten as the proximal parts of the guide posts 91, 92 telescope into the distal parts of the guide posts 91, 92 (or the distal parts telescope into the proximal parts). The guide posts 91, 92 may be manufactured with sufficient strength to avoid bending, particularly at their fixed bases. It is advantageous to prevent the guide posts 91, 92 from extending significantly beyond the distal side of the window D in order to avoid having the guide posts 91, 92 block the chain saw from cutting laterally or to avoid having the guide posts 91, 92 block advancement or other positioning of the chain saw.

Figure 9A:
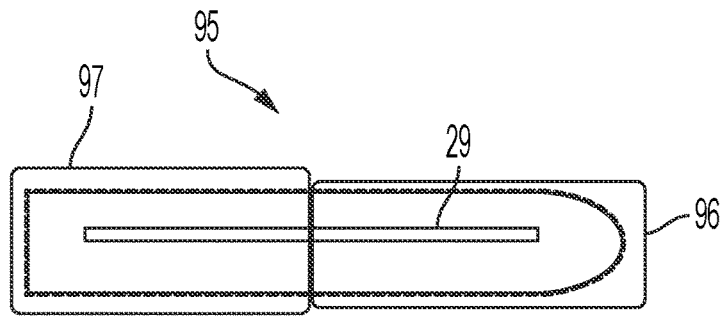
FIG. 9A shows an example embodiment of a chain saw with a protective cover in accordance with the disclosure.
Figure 9B:
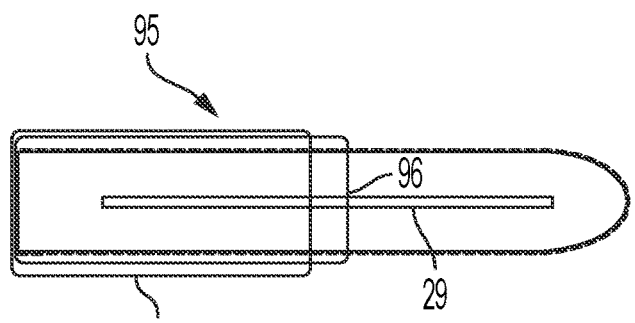
FIG. 9B shows the embodiment of FIG. 9A with the protective cover in a retracted condition.

FIGS. 9A and 9B show another embodiment for use with a cutting guide or block C. The chain saw includes a cover 95 that acts as a block laterally but also passes over and under the saw bar to guard directly against contact with the window D on all four sides. In some embodiments this cover 95 may be strengthened by a connection between its upper and lower surfaces that passes through a slot 29 in the saw bar. Like the guide posts 91, 92, the cover 95 may be collapsible, with a distal part 96 telescoping into a proximal part 97, or vice versa. The distal part 96 of the cover 95 may have one or more stops to prevent distal movement past a desired point, at which further advancement of the saw causes shortening of the cover 95 by the telescopic collapsing of the distal part 96 and the proximal part 97, as shown in FIG. 9B.

Figure 9C:
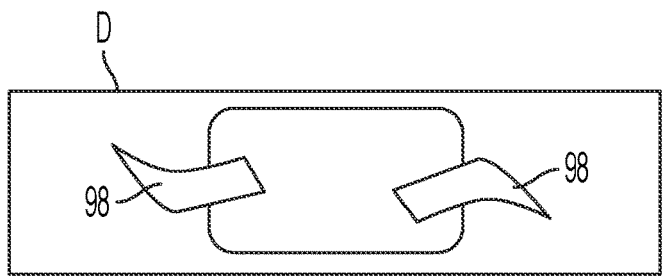
FIG. 9C shows an example embodiment of a chain saw with cutting elements in a retracted condition.
Figure 9D:
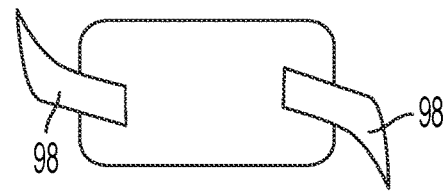
FIG. 9D shows the embodiment of FIG. 9C with the cutting elements in an extended condition.

FIGS. 9C and 9D show another embodiment for use with a cutting block C. In this embodiment, the cutting elements 98 of the saw links retract or rotate medially when they are in the window D, as shown in FIG. 9C. Those cutting elements 98 that have passed through the window D can splay outward, as shown in FIG. 9D. The outward movement can happen either automatically, such as by spring action, or due to contact with bone.

Figure 9E:
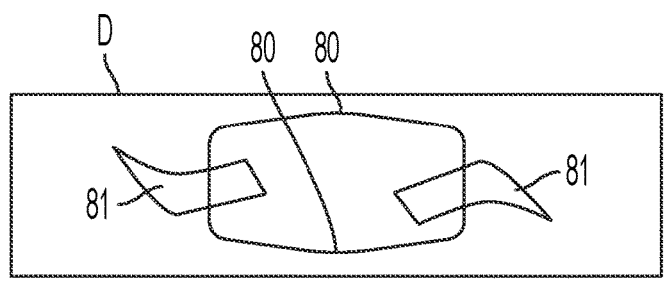
FIG. 9E shows an example embodiment of a chain saw bar for fitting through a cutting guide.

FIG. 9E shows another embodiment for use with a cutting block C. In this embodiment, the chain saw bar has cambered sides 80. The cambered sides 80 of the saw bar prevent the cutting elements 81 from contacting the inner surfaces of the window D of the cutting block C. The body of the saw bar, at the cambered sides 80, is close to the inner surfaces of the window D, which keeps the saw in a stable position with minimal pitching within the window D and prevents the cutting elements 81 from contacting the inner surfaces of the window D.

In certain variations, the saw bar may be manufactured to fit the window D, for instance with a pressed fit, running fit, or slip fit. Some clearance around the saw bar allows the links to pitch at a small angle. One embodiment is to have a close fit between the height of the guide opening and the width of the saw. At the same time, the friction of passing the saw through the guide must be minimized. The bar may also be spring loaded or covered with a deforming layer such that the bar will be stabilized within the window D but still will be able to move. The bar may be covered with a sheath that does not extend beyond the cutting block C. The links may be coated with titanium nitride or similar material to minimize any galling or debris that would result if the links (e.g., of stainless steel) contacted the cutting block C.

The guide posts 91, 92, the cover 95, or other similar longitudinal slides or stabilizing guards could be computer controlled or controlled remotely, such as by pneumatic, electromechanical, or other actuators. The posts, cover, slides, or guards may also have a feedback system so that the computer or operator knows their position. They may also include fiber optics or fiber optic cameras to assist in visualization. This is facilitated by the reduced vibration of embodiments of chain saws disclosed herein, as compared to high vibrations with sagittal saws that would make visualization via such components difficult or impossible. The posts, cover, slides, or guards may also be used to coordinate the lavage to keep the visual field clear.

The protective elements, such as the posts, cover, slides, or guards described above, prevent the rotating chain and the saw bar from contacting the walls of the slot of the cutting block or guide while preserving the guidance function of the slot. Thus, the protective elements help with the alignment of the chain saw while preventing disadvantageous movement of the chain saw or disadvantageous contact between the chain saw and cutting block or guide.

Figure 10:
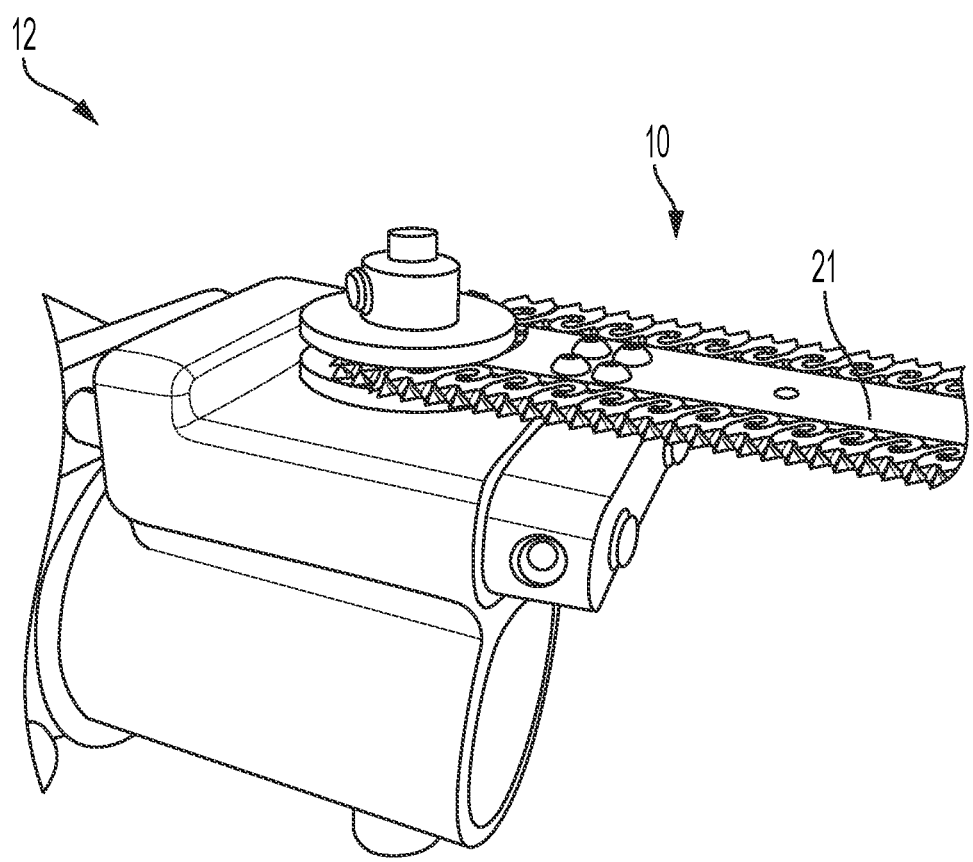
FIG. 10 shows an example of a chain saw in accordance with the disclosure, showing an attachment of a chain saw driving head to a chain saw cartridge.

FIG. 10 shows an example of a chain saw, showing an attachment of a chain saw driving head 12 to a chain saw cartridge 10. The saw bar 20, 21 is attached to the driving head 12 with fasteners through the holes 23 for the suspension system (see FIG. 4A). The driving head 12 has a driving rotor, rotated by a motor, that engages with the driving recess 77 of the drive cog assembly 70 to drive the chain of the chain saw.

The chain saw may include various components for driving the chain of the chain saw. The chain saw may include a motor, e.g., a DC or AC motor, or an engine that generates power. The chain saw may further include a drive mechanism that transmits power from the motor or engine to the chain. The chain may be controllable at variable speeds and torque.

Chain saws and/or chain saw components as described herein have advantages over certain prior art chain saws and components. One issue common to most prior chain saws is stability of the chain and its links as it moves along the bar and when it is subject to forces while cutting. The chain moves rapidly along the guide at the border of the bar. When interacting with material during cutting, it is subject to forces that promote movement of the links out of their normal position. Partly this is due to the shape of the cutting element, which often has cutting edges at the top and side, as shown in FIG. 11A, which shows a link from a typical prior art chain saw. The two cutting edges generate a variety of forces that tend to cause the link to move as it moves along the guide G of the bar, shown in FIG. 11B. FIG. 11B shows a cross-sectional view of a prior art link in a normal position; FIG. 11C shows a cross-sectional view of a prior art link in a laterally displaced position; FIG. 11D shows a cross-sectional view of a prior art link in a tilted position; FIG. 11E shows a side view of a prior art link; and FIG. 11F shows a top view of a prior art link. The two cutting edges of the link generate a variety of forces that tend to cause the link to move laterally as shown in FIG. 11C, to tilt as shown in FIG. 11D, to pitch as shown by the arrow in FIG. 11E, and/or to rotate as shown by the arrow in FIG. 11F. In addition, the cutting elements of sequential links often face in opposite directions. These movements place high stresses on the connections between links as well as the mechanical interaction between the links and the guide G. These stresses can cause failure of components. Therefore, the components need to be made relatively large and bulky, making this prior art design impractical for surgical use.

One advantage of certain embodiments of links as described herein, such as a link as illustrated in FIG. 2, is that the cutting elements are designed to exert force primarily in the same plane as the saw bar. This produces primarily a single force vector pushing the link toward the bar, where the bar can resist the normal force. For simplicity, this vector, normal to the chain path and directed toward the bar, will be called vertical. This avoids the eccentric forces acting on the links of most prior chain saws, results in less stress on chain elements thereby allowing the chain design to be optimized for other aspects of the cutting process and minimizing chain failure, and results in decreased vibration and increased control over the chain saw cuts by humans as well as robots.

FIGS. 12A-12D illustrate potential cutting element profiles for limiting the cutting element forces to being exerted primarily in the same plane as the bar. FIG. 12D is a schematic illustration analogous to the cutting teeth 60 in FIG. 2. The shape and positioning of the cutting elements cause the lateral forces to balance out, leaving a net force vector vertical into the bar. In FIG. 12A, the conical, e.g., pyramid-shaped, cutting elements are arranged on three sides, i.e., the top and two lateral sides of the link. Again, the lateral forces balance out, leaving a net force vector vertical into the bar. In FIG. 12B, the link itself has a top with two sloped surfaces, and the conical, e.g., pyramid-shaped, cutting elements are arranged on the two sloped surfaces at the top of the link. As in FIG. 12A, the lateral forces balance out, leaving a net force vector vertical into the bar. In FIG. 12C, a series of conical, e.g., pyramid-shaped, cutting elements are arranged on the top of the link. As in FIGS. 12A and 12B, the lateral forces balance out, leaving a net force vector vertical into the bar. In FIG. 12D, like in FIG. 2, a series of conical, e.g., pyramid-shaped, cutting elements are arranged on the top of the link, with one row of cutting elements along one lateral side of the link and another row of cutting elements along the other lateral side of the link. As in FIGS. 12A-12C, the lateral forces balance out, leaving a net force vector vertical into the bar.

Another advantage of a link as illustrated in FIG. 2 and various other links described herein is that the shapes of the vertical cutting elements result in improved cutting and surgical outcomes. The shapes permit straight cuts, facilitate removal of bone debris, and allow a decrease in chain speed which minimizes friction and tissue damage. The shapes can also allow cutting in both directions of chain movement.

In the example of FIG. 2 and various other embodiments described above, the cutting elements have a pyramidal shape. The pyramidal elements are able to cut bone with their peaks and remove bone debris with their valleys. The peaks are relatively close to each other such that during cutting the bone is impacted by small cutting elements at short time intervals, thereby minimizing vibration. In contrast, long time intervals between impacts of cutting elements can cause abrupt increases in impact force that result in saw vibration.

Another contributing factor to vibration is the cutting element shape. Cutting elements on wood-cutting chain saws have sharp chisel-shaped cutting edges. These cutting elements shave off a piece of material. These chisel-shaped cutting elements as in wood-cutting saws impact bone harder than thin pyramidal teeth as disclosed herein. In addition, the sharp point tips of the pyramids disclosed herein get an immediate purchase on, or hold in, bone, even if approached at an angle. In contrast, many other saw designs often jump to different spots when first applied to bone.

Most chain saws rotate in one direction and have their cutting elements oriented in that direction. Movement of the chain in the direction of the cutting edge is necessary, while movement in the opposite direction does not cut. One reason is that cutting some substances such as wood requires a relatively complex cutting configuration with multiple components. When a fallen tree is cut from the top side, only the bottom of the chain saw bar can be used. When the chain saw is then used to cut the undersurface of the log, the saw must be flipped around such that the former bottom of the bar faces up. As most saws are designed to be held in one ergonomic position, cutting the bottom of a log can be dangerous.

In bone surgery, it is an advantage to be able to cut in both directions. In some embodiments disclosed herein, such as that shown in FIG. 2, the cutting surface comprises symmetric elements, allowing similar cutting action when the chain moves in either direction. In this case the cutting effect is the same in both directions of chain movement. In alternate embodiments, the cutting elements may have cutting surfaces in both directions but may be asymmetric, one side having a more aggressive configuration than the other. For example, the cutting teeth may be pyramidal in shape with sharper cutting edges in one direction than in the opposite direction. Asymmetric cutting teeth can perform different functions in opposite directions.

Cutting in both directions, or bidirectional cutting, can be useful for removing debris, which can interfere with the efficiency and directional control of the bone saw. Specifically, a saw cutting to the right can have the cutting edge moving toward the operator (clockwise), which clears debris efficiently. A chain cutting toward the left side removes debris better when the chain moves in a counterclockwise direction, again clearing the debris toward the operator. Thus, in accordance with certain embodiments of the invention that facilitate bidirectional cutting, the cutting saw links can be directed toward the operator regardless of whether the saw is cutting to the right or to the left. In addition, it can be easier for the operator to control a saw when the cutting forces are the same on both sides. Also, when approaching sensitive tissue, it can be desirable to have the chain at the cutting surface rotating away from the operator so as to avoid unintentionally driving the saw toward the sensitive tissue. A chain saw with bidirectional cutting allows switching between cutting directions as desired.

Asymmetric cutting teeth can be useful for cutting different types of bone or tissue. Bone hardness varies significantly in different areas. A single type of cutting configuration may not cut all types of bone efficiently. As an extreme example, the outside of a long bone is made of very hard bone called cortical bone. Cortical bone performs the weight-bearing function of long bones. In contrast, the inside of long bone contains bone marrow where blood cells are formed. This substance, called cancellous bone, is very soft and is closer to soft tissue in its consistency. Ideally these types of bone would be cut with saws adapted to their different qualities. Instead of two saws, a single saw as disclosed herein with asymmetric cutting teeth that cut differently depending on chain direction can be used. In one direction, the links can have more aggressive cutting teeth surfaces, such as for cutting cortical bone, and in the opposite direction the links can have less aggressive cutting teeth surfaces, such as for cutting cancellous bone.

In addition, the surgical field around an exposed joint often has strands of unwanted soft tissue such as ligaments that overlap into the bone cutting field. As a result, in current sagittal saw procedures, the surgeon needs to remove the saw from the field and switch to different instruments, such as scissors or scalpels, to cut this soft tissue. This can be extremely time wasting, particularly with robotic systems where the entire system may need to be repositioned each time. Instead, a chain saw as disclosed herein may have more aggressive bone cutting elements facing in one direction of chain movement and less aggressive soft tissue cutting elements facing in the other direction.

Another problem faced by surgeons is the presence of arteries and nerves lying directly on the surface of bone. When cutting long bones for knee replacement these structures are present behind the cortical bone in the very depths of the operative field. Cutting cortical bone in this area with aggressive cutting instruments can easily penetrate the cortical bone and cause catastrophic damage. In these situations, a chain saw as disclosed herein can work as an oscillating saw. The chain saw could be switched into oscillating mode, rapidly alternating the direction of chain movement so that the chain moves back and forth rapidly over a very small distance, i.e., a very small stroke or travel of the chain. This can result in cutting the bone as desired while avoiding cutting tissue that is to remain intact. For example, if perforation through the back wall of bone occurs, it causes minimal damage to soft tissue.

For moving the chain with very short strokes in an oscillating motion with high frequency, the chain can be driven ultrasonically. High frequency motion can generate heat. For this or other embodiments, one or more temperature sensors may be embedded into the chain saw, such as in the saw bar.

Further advantages of certain chain saws as disclosed herein result from the interface between the saw bar and the links. One such example is described above in relation to FIGS. 5A-5C, showing a bar 21 with a rail 30 extending from the main body 22 of the bar 21. As described above, the links 40 have grooves 55 in them so that the links 40 fit over and straddle the rail 30.

Figure 13A:
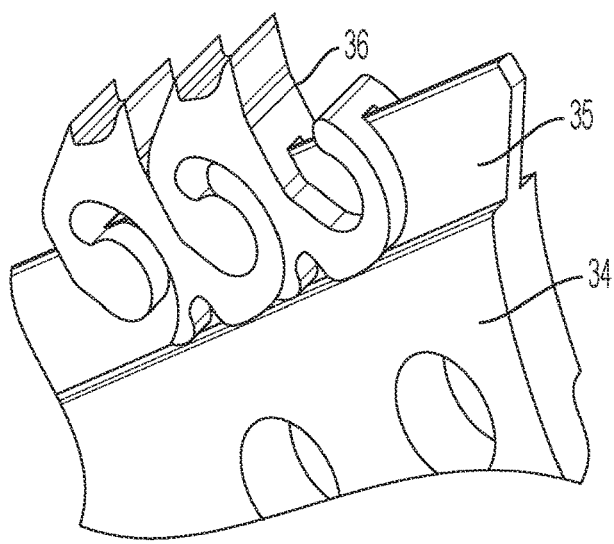
FIG. 13A shows another example of a saw bar with a rail with links that have grooves for fitting the links over the rail.
Figure 13B:
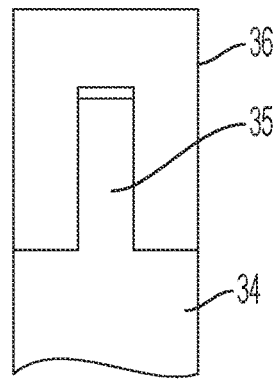
FIG. 13B shows a schematic illustration of the embodiment of FIG. 13A.

FIG. 13A shows another example of a bar 34 with a rail 35. The links 36 have chisel-shaped cutting elements and grooves for fitting the links over the rail 35, such that the links 36 straddle the rail 35. FIG. 13B shows a schematic illustration of the bar 34, rail 35, and link 36.

Figure 13C:
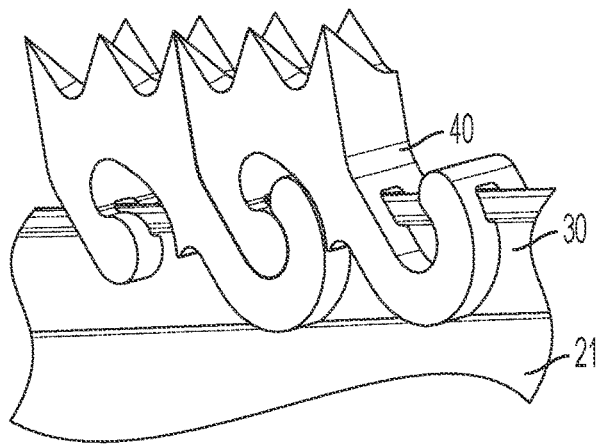
FIG. 13C shows another view of the embodiment shown in FIGS. 5A-5C.
Figure 13D:
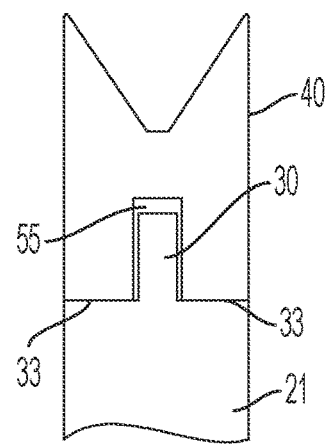
FIG. 13D shows a schematic illustration of the embodiment of FIG. 13C.

FIG. 13C shows another view of the embodiment shown in FIGS. 5A-5C. FIG. 13D shows a schematic illustration of the bar 21, rail 30, and link 40 (the projection 32 is not illustrated in FIG. 13D).

In these embodiments, stability is enhanced by how the links interface with the bar. Lateral dislocation of the links is prevented, and the lateral stability of the chain saw is increased, by the novel design in which the links straddle a single rail of the saw bar. These embodiments give greater strength to the entire mechanism and allow greater flexibility in design.

One advantage of these embodiments is that links are less likely to lean or rock laterally in contrast to a saw chain in which the bar has a gutter and the links ride in the gutter (e.g., FIG. 11B). In addition, the width of the link section above the saw bar can be larger (as compared to a saw chain in which the bar has a gutter and the links ride in the gutter, e.g., FIG. 11B), thereby increasing the area of interlocking engagement between adjacent links. The increased width also allows for more flexibility in cutting edge designs. Moreover, with the monorail design, resistance to lateral displacement and to pitching of the links is increased. Another advantage is that the design simplifies the bar and decreases the stresses that the bar could otherwise experience. This allows the bar to be made of a variety of materials, including very hard plastics, such as Corian or other plastics. As a result, the bar can be manufactured more cost effectively, such as by injection molding. Some materials that the bar design enables, such as certain plastics, provide increased lubricity, thereby reducing friction.

In other embodiments, the bar could be made from a dielectric material and the chain could be energized to be used as an electrocautery system. Such a chain saw system could be used to cauterize blood vessels, which would help prevent excessive blood loss.

In an embodiment such as that shown in FIG. 13D, due to the clearance between the rail 30 and the groove 55, the vertical load from the links 40 is transmitted from the links 40 directly to the skids or ledges 33 of the saw bar 21 on either side of the rail 30. Thus, the normal forces from the links 40 are taken up by the main body of the saw bar 21 as opposed to the rail 30 itself.

Figure 13E:
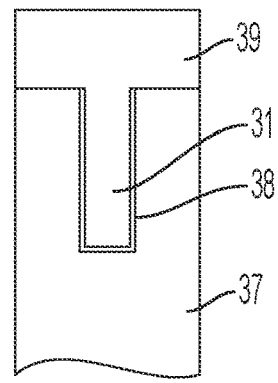
FIG. 13E shows a schematic illustration of another example of a saw bar with links.

FIG. 13E shows a schematic illustration of another example of a bar 37 with links 39. In this example, the links 39 have downwardly-projecting ridges 31 that fit into a corresponding slot 38 in the bar. The ridges 31 act like a keel, providing stability to the links 39. The embodiment of FIG. 13E results in strong links 39 guided along the bar 37. In a variation, the ridges 31 may have a laterally-extending projection (like projection 32) that fits in a complementary laterally-indented notch (like notch 57) in the bar 37 in the side of the slot 38. In another variation, the wall of the slot 38 may have a laterally-extending projection (like projection 32) that fits in a complementary laterally-indented notch (like notch 57) in the side of the ridges 31. These variations (with interlocking projections and notches) provide a similar link lock or retention element as described above, preventing the links 39 from coming off of the bar 37 in a direction away from the bar.

Further advantages of certain chain saws as disclosed herein derive from the link lock mechanism. An example is the use of a projection 32 and corresponding notches 57 as disclosed above.

In certain prior art chain saws, if the chain were to break while cutting the links would come off the chain as individual pieces. The inertia of an individual link may not result in any significant harm by itself; however, these pieces would need to be removed from the operative field. This can be difficult in the depths of a bone cut or in soft tissue. In addition, some pieces may fall out of the surgical field and onto the drapes so they could be very difficult to find.

One solution is that the links could be made magnetic. Loose links could be gathered by a magnet, facilitating their collection.

To prevent loss of links in the event of a chain break, a link lock mechanism as disclosed herein may be used. One embodiment of a link lock is a projection from the rail as disclosed above or other guide elements that would serve to retain the links. As seen in FIGS. 5A-5C, even a small projection prevents the links from detaching from the rail. The projection may be symmetrical or asymmetrical. The projection does not need to go around the entire saw bar but may be only in some parts of the saw bar.

The retaining projection also has a further advantage. Normally a chain saw running at working speed is subject to forces when it passes around the curves at each end of the saw bar. The shape of the typical chain along the long sides of the saw is not straight but bows outward. Cutting with a typical saw thereby tends to make a slightly curved shape. With a link lock mechanism as disclosed herein, such as a projection 32 and corresponding notches 57, the chain is held against the bar, thereby preventing this unwanted bowing. The result is a cut with a straight lateral border.

Chain saws as disclosed herein may incorporate additional elements for safety or other functionality. For example, chain saws as disclosed herein may include a torque limiting device, for example an electronic torque limiter through the motor or a slip clutch incorporated into the drive train. As other examples, torque limiting can be incorporated by monitoring the current and therefore the power transmitted to the drive train, by a frictional clutch, or by a torque limiting device using a detent and spring-loaded pawl, or other torque limiting mechanisms.

A further advantage of certain embodiments of chain saws disclosed herein is that the chain saw designs facilitate precision bone cutting, which enables improved, closer, or tighter fits between bone and implant. The precise fit locks the implant in place better, reducing risk of displacement and promoting faster healing. This closer fit can result in better short-term and long-term patient outcomes. For example, an improved fit can allow for an implant that can support stresses more rapidly. This could allow a patient to walk sooner after surgery with a lower risk of damaging the implant tissue interface. Bone growth and union between an implant and the surrounding bone needs to occur eventually. Precise fitting surfaces as achievable by embodiments disclosed herein accelerate this healing process.

In addition, with the precise cutting enabled by embodiments disclosed herein, implant indications are achievable that cannot be treated at present. Certain embodiments of the invention also facilitate more custom implantations.

FIG. 14 illustrates an example of an application of precise cutting achievable with certain embodiments. FIGS. 14A-14B show an example shaped implant Y for a vertebra. FIG. 14C shows a vertebra V with an excavated volume X having a precise stepped-up shape, achievable with certain embodiments of the invention, for receiving the implant of FIGS. 14A-14B. The implant Y can be manufactured with a shape corresponding to the excavated volume X. In this example, the step up in the implant Y will lock it in place in the anterior to posterior direction. The ledge shape of the implant Y stabilizes it in the superior to inferior direction.

Figure 14A:
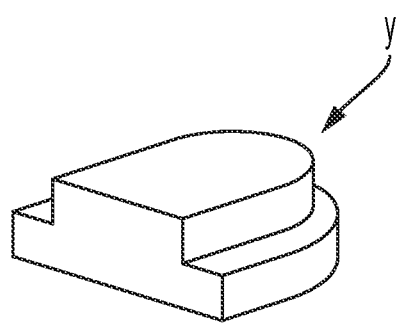
FIG. 14A shows a top perspective view of an example shaped implant for a vertebra.
Figure 14B:
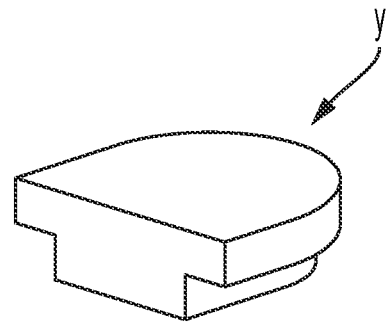
FIG. 14B shows a bottom perspective view of the implant of FIG. 14A.
Figure 14C:
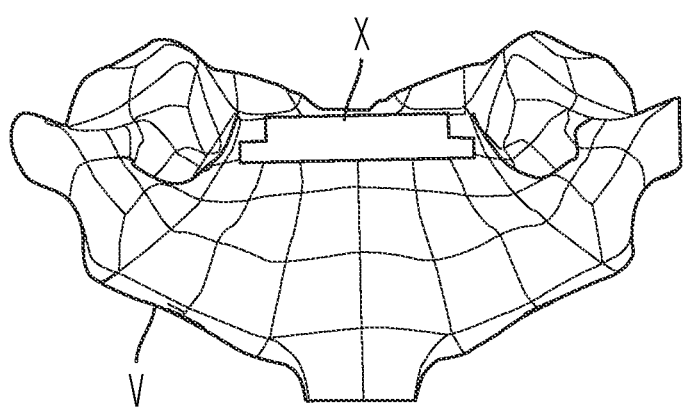
FIG. 14C shows a vertebra with an excavated volume having a precise shape, achievable with certain embodiments of the invention, for receiving the implant of FIGS. 14A-14B.
Figure 14D:
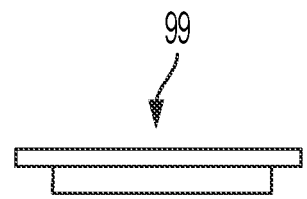
FIG. 14D shows a front view of a custom saw bar for cutting the shaped bone space of FIG. 14C in accordance with certain embodiments of the invention.

A precise space such as the volume X can be made with a chain saw as described above. For example, the chain saw cartridge 10 can be used for precisely cutting such a space. In other examples, the links or saw bar may be shaped for making the shaped space. The links of the saw can have custom outlines to make proper excavated shapes for correspondingly-shaped implants. For example, in a link with two rows of teeth wherein a first row of teeth is along a first lateral side and a second row of teeth is along a second lateral side, the first row of teeth may be higher than the second row of teeth. A chain of such links may be used for excavating a stepped-up shape as in FIG. 14C, with the higher row of teeth excavating the wider part and the lower row of teeth excavating the narrower part. In an alternative, the links may have teeth that are higher in the middle than the lateral sides, and the teeth may be rounded, for creating convexly curved sides of the excavated space. In another alternative, the links may have teeth that are higher along the lateral sides than in the middle, for creating concavely curved sides of the excavated space. In another alternative, FIG. 14D shows a front view of a custom saw bar 99 that allows the shaped bone space of FIG. 14C to be made with a single plunge cut. Multiple chains may be driven simultaneously around the same saw bar, one along the wider part of the bar and one along the narrower part of the bar. The shape of the cutting profile of the links and/or the saw bar can be customized to the implant so that a single pass of the chain saw can produce an extremely stable, repeatable, and intimate fit to an implant. The saw and/or cutting profile of the links can be custom designed to produce the form required for the implant.

The improved fit between the bone or other tissue and the implant helps improve patient outcome. An implant with a better fit has a lower risk of displacement and can support stresses more quickly. The patient can regain mobility sooner with a lower risk of damage to the tissue-implant interface.

Figures 15A, 15B:
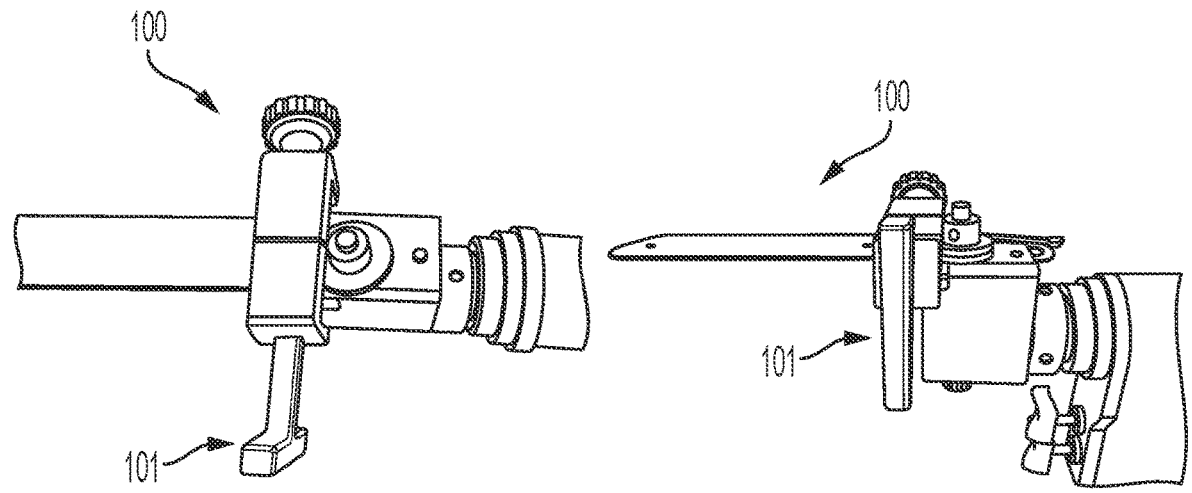
FIG. 15A shows a top view of an example of a chain saw with a surgical handle.
FIG. 15B shows a side perspective view of the chain saw with surgical handle of FIG. 15A.
Figure 15C:
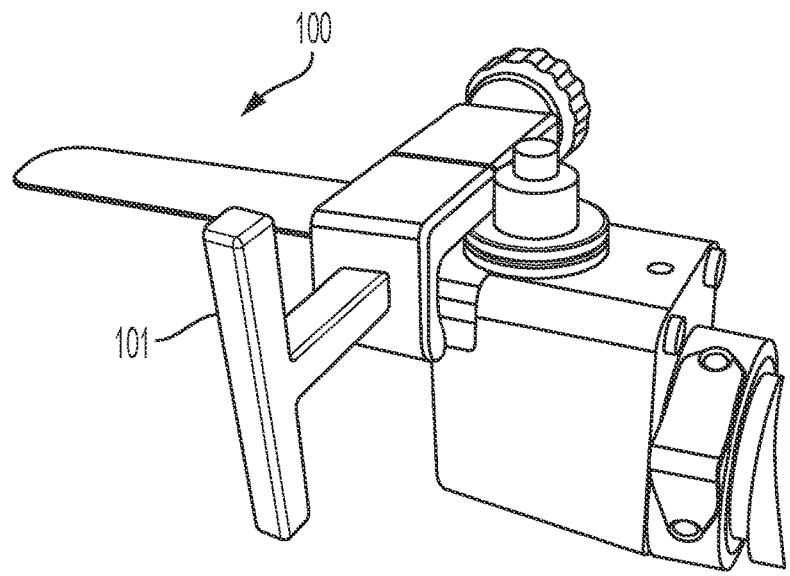
FIG. 15C shows a rear perspective view of the chain saw with surgical handle of FIG. 15A.

FIGS. 15A-15E show an example of a chain saw 100 with a surgical handle 101. The chain saw 100 may be similar to chain saws as described above. The surgical handle 101 may be attached to the saw mechanism such that linear sideways or lateral movements can be performed more accurately with hand movement. The surgical handle 101 may be removably attached to the saw mechanism. In the illustrated example, the surgical handle 101 projects laterally from the saw mechanism and has protuberances that can be easily grasped by the user (surgeon). By holding onto the handle 101, the surgeon can move the chain saw blade laterally in the plane of the blade to the left (FIG. 15D) or to the right (FIG. 15E). The chain saw blade may be pivotable about an axis of rotation.

FIG. 16 shows a guard 110 that can be attached to a chain saw 100. The chain saw 100 may be similar to chain saws as described above. The guard 110 may be attached around one longitudinal side and the distal end of the chain saw to guard the chain in those areas. In alternate embodiments, the guard may be designed to cover more or less of the chain path, such as extending only along one longitudinal side, while leaving the distal end uncovered. In cases where only one part of the chain saw is used for cutting, such as one longitudinal side, the guard 110 can prevent unwanted cutting, such as inadvertent tissue damage from the other longitudinal side of the chain saw. The guard 110 may be removable. The guard 110 may also be reversible, to guard the other side of the saw. In the illustrated embodiment, the guard 110 has a U-shaped base on one end. Each arm of the U can be placed within a tubular restrainer attached to the chain saw. Double anchoring can stabilize the device. On one side, the guard 110 extends along the length of the cutting chain.

Figure 17A:
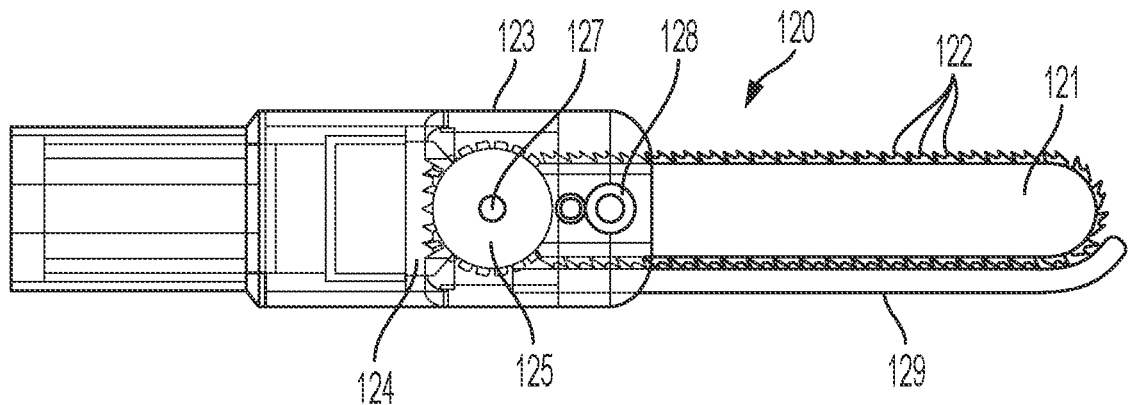
FIG. 17A shows a top view of an example embodiment of a drive train mechanism for a chain saw in accordance with the disclosure.
Figure 17B:
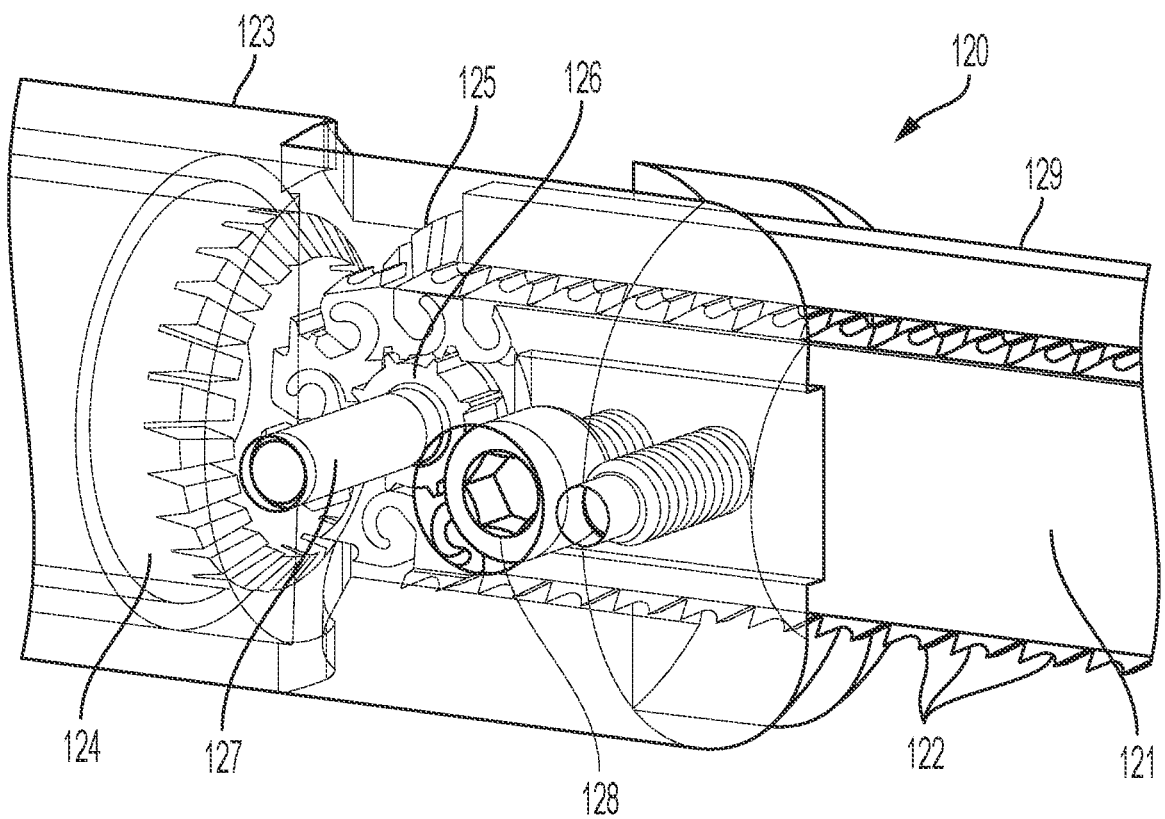
FIG. 17B shows an enlarged bottom perspective view of the drive train mechanism of FIG. 17A.

FIGS. 17A-17B show an example embodiment of a drive train mechanism for a chain saw 120. The chain saw bar 121 and links 122 may be similar to one or more of the chain saw bars and links as described above. A housing 123 is shown as transparent in FIGS. 17A-17B in order to show the details of the drive train mechanism.

As can be seen in FIGS. 17A-17B, a drive gear 124 interfaces with a saw gear 125 at 90 degrees. The drive gear 124 may be driven by a suitable driving mechanism such as a motor as described above. The drive gear 124 and the saw gear 125 may be bevel gears that engage with each other. Rotation of the drive gear 124 results in rotation of the saw gear 125. In the illustrated example, the axis of the drive gear 124 is aligned with the axis of the saw bar 121. In alternative embodiments, the axis of the drive gear 124 need not be aligned with the axis of the saw bar 121. For example, the axis of the drive gear 124 may be at a 90 degree angle with the axis of the saw bar 121.

The saw gear 125 is firmly coupled to a chain drive cog 126 such that rotation of the saw gear 125 causes rotation of the chain drive cog 126. In this example, the saw gear 125 and the chain drive cog 126 are both firmly attached to an axle 127 that passes from side to side of the housing 123 and freely rotates with respect to the housing 123. Thus, in this example, the saw gear 125 is firmly coupled to the chain drive cog 126 through the axle 127. In other examples, the saw gear 125 may be directly coupled to the chain drive cog 126. The saw gear 125 and chain drive cog 126 may rotate about a fixed axle.

The chain drive cog 126 interfaces with the inner edge of the chain of links 122 such that the cog teeth of the chain drive cog 126 interface with drive cog engagement recesses on the chain links 122. Thus, rotation of the chain drive cog 126 causes rotation of the chain. The chain drive cog 126 may be similar to the drive cog 72 discussed above.

In the example of FIGS. 17A-17B, one or more set screws 128 can be used to stabilize the saw bar 121. Also, a protective guard 129 may be used to cover the teeth of the chain on one side of the chain saw, thereby protecting adjacent tissue from being inadvertently damaged. The protective guard 129 may be similar to the protective guard 110 discussed above.

Figure 18A:
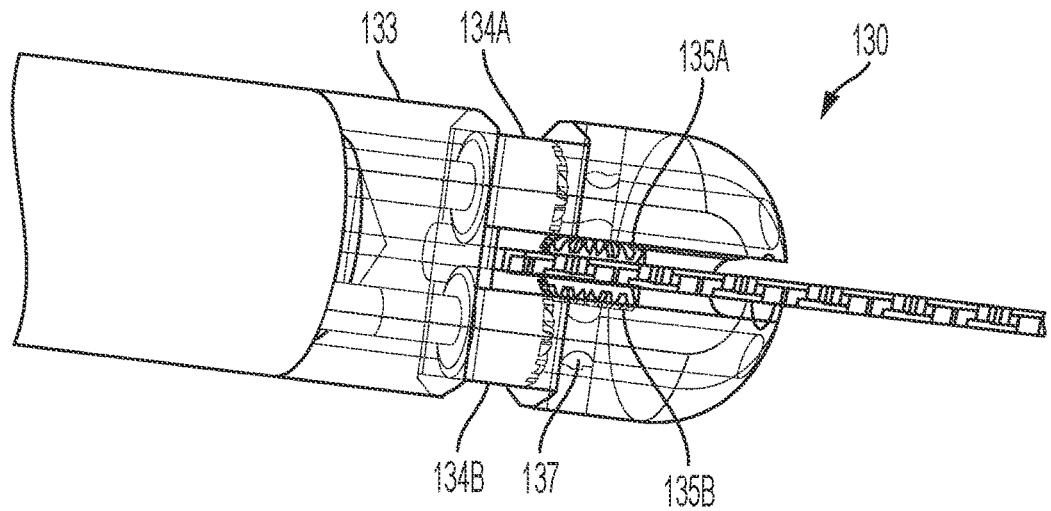
FIG. 18A shows an edge view of another example embodiment of a drive train mechanism for a chain saw in accordance with the disclosure.
Figure 18B:
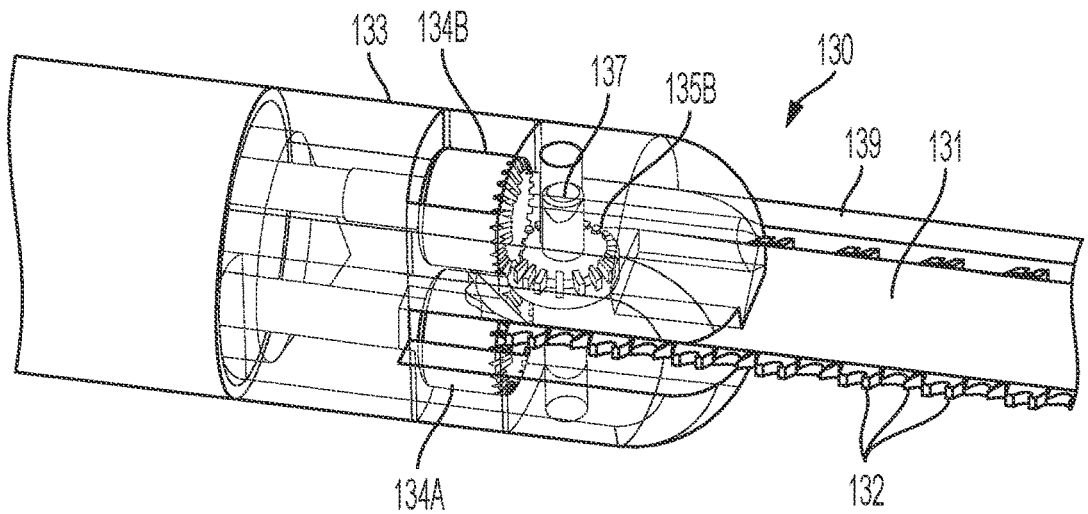
FIG. 18B shows an oblique view of the drive train mechanism of FIG. 18A from a first side of the chain saw.
Figure 18C:
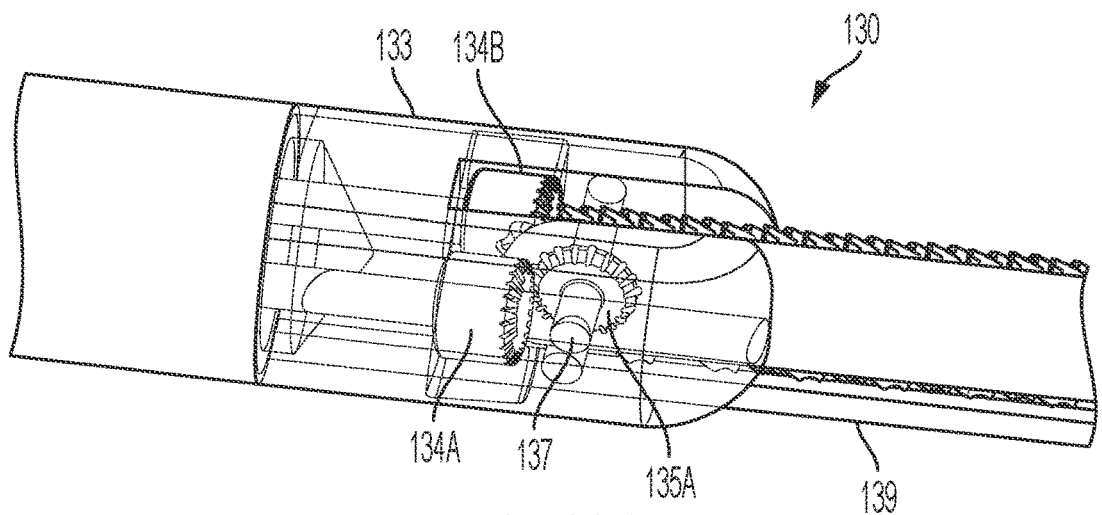
FIG. 18C shows an oblique view of the drive train mechanism of FIG. 18A from a second side of the chain saw.

FIGS. 18A-18C show another example of a drive train mechanism for a chain saw 130. The chain saw bar 131 and links 132 may be similar to one or more of the chain saw bars and links as described above. A housing 133 is shown as transparent in FIGS. 18A-18C in order to show the details of the drive train mechanism.

The example embodiment of FIGS. 18A-18C has a saw position drive gear 134A and a chain drive gear 134B. Each of the drive gears 134A, 134B interfaces with a saw gear 135A, 135B, respectively. Each drive gear 134A, 134B and its respective saw gear 135A, 135B may be bevel gears that engage with each other. Rotation of each drive gear 134A, 134B results in rotation of its respective saw gear 135A, 135B. In the illustrated example, the axis of each drive gear 134A, 134B is parallel to the axis of the saw bar 131. In alternative embodiments, the axes of the drive gears 134A, 134B need not be parallel to the axis of the saw bar 131. For example, the axes of the drive gears 134A, 134B may be at a 90 degree angle to and offset from the axis of the saw bar 131.

The chain drive gear 134B is used for driving the chain around the saw bar and may be driven by a suitable driving mechanism such as a motor as described above. The saw gear 135B may be firmly coupled to a chain drive cog (not shown) such that rotation of the saw gear 135B causes rotation of the chain drive cog. In one example, the saw gear 135B and the chain drive cog are firmly attached to an axle 137 that passes from side to side of the housing 133 and freely rotates with respect to the housing 133. Thus, in such an example, the saw gear 135B is firmly coupled to the chain drive cog through the axle 137. In other examples, the saw gear 135B may be directly coupled to the chain drive cog (and the axle may or may not rotate).

The chain drive cog interfaces with the inner edge of the chain of links 132 such that the cog teeth of the chain drive cog interface with drive cog engagement recesses on the chain links 132. Thus, rotation of the chain drive cog causes rotation of the chain. The chain drive cog may be similar to the drive cog 72 discussed above.

The saw position drive gear 134A is used for positioning the saw bar and may be driven by a suitable driving mechanism such as a motor (e.g., a stepper motor). The saw gear 135A may be firmly coupled to the saw bar such that rotation of the saw gear 135A causes rotation of the saw bar about the axis of the axle 137. In one example, the saw gear 135A and the saw bar are firmly attached to the axle 137, and the axle 137 rotates with the saw bar. In another example, the saw gear 135A and the saw bar rotate around the axle 137.

By control of the saw position drive gear 134A, the user can pivot the saw bar to a desired angle around the axis of the axle 137. Thus, the drive mechanism of FIGS. 18A-18C can be used both for driving the chain around the saw bar as well as for pivoting the saw bar.

In the example of FIGS. 18A-18C, a protective guard 139 may be used to cover the teeth of the chain on one side of the chain saw, thereby protecting adjacent tissue from being inadvertently damaged. The protective guard 139 may be similar to the protective guard 110 discussed above.

Some embodiments of inventions described herein are useful for various surgical applications. One such application is minimally invasive surgery. Currently, many surgical specialties perform minimally invasive surgery. Large incisions have high levels of post-operative pain and morbidity. In minimally invasive surgery, surgeons operate through several small incisions. They pass cannulas through these incisions, essentially tubes which pass into the body. Using specialized instruments through the cannulas, surgeons can operate without the disadvantages of large incisions.

Another surgical advance has been the use of robotics during surgery. Robots can operate in small spaces with greater precision than humans. However, certain existing instrument such as oscillating bone saws have too much vibration to be controlled efficiently by current robot technology. The result is that orthopedics, a specialty that could benefit greatly from precise bone cutting and shaping, has been limited in its ability to take advantage of robotic technology.

A clear need exists for a small bone saw that can pass through a cannula, and which also has little vibration. Certain embodiments of chain saws as disclosed herein can pass through a relatively small cannula, e.g., with 10 mm or less interior diameter, and can cut bone with little vibration.

Figure 19:
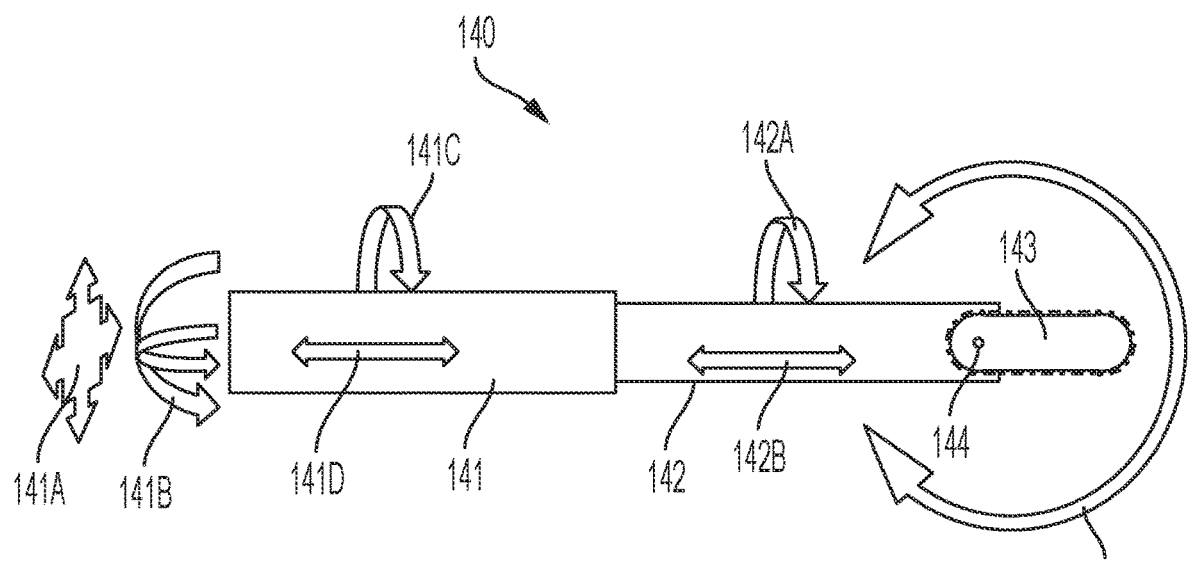
FIG. 19 shows an illustration of an example mechanism for controlling motion of a chain saw.

FIG. 19 shows an illustration of an example mechanism 140 for controlling motion of a chain saw. The mechanism 140 comprises a robotic arm 141 that can be moved in any direction in a plane perpendicular to the long axis of the chain saw, as indicated by arrows 141A. From a fixation point at its proximal end, the robotic arm 141 can tilt at various angles up to highly obtuse angles in any direction, as indicated by arrows 141B. The mechanism 140 may be repositioned to have the fixation point of the robotic arm 141 at any desired location. The robotic arm 141 also can rotate at any angle around its long axis, as indicated by the arrow 141C. The robotic arm 141 also can extend and retract, as indicated by the arrow 141D. A tubular extension 142 extends from the robotic arm 141. The tubular extension 142 is part of the device that enters into the body. Like the robotic arm 141, the tubular extension 142 can rotate at any angle around its long axis, as indicated by the arrow 142A, and can extend and retract, as indicated by the arrow 142B. The saw blade 143 can pivot around a pivot axis 144 in relation to the tubular extension 142 up to 360 degrees, as indicated by arrow 143A. All of these positions and motions may be performed by computer control of robotics. The mobility of the robotic arm 141 allows for almost unlimited mobility of saw placement and angulation, as shown in FIG. 19.

Figure 20A:
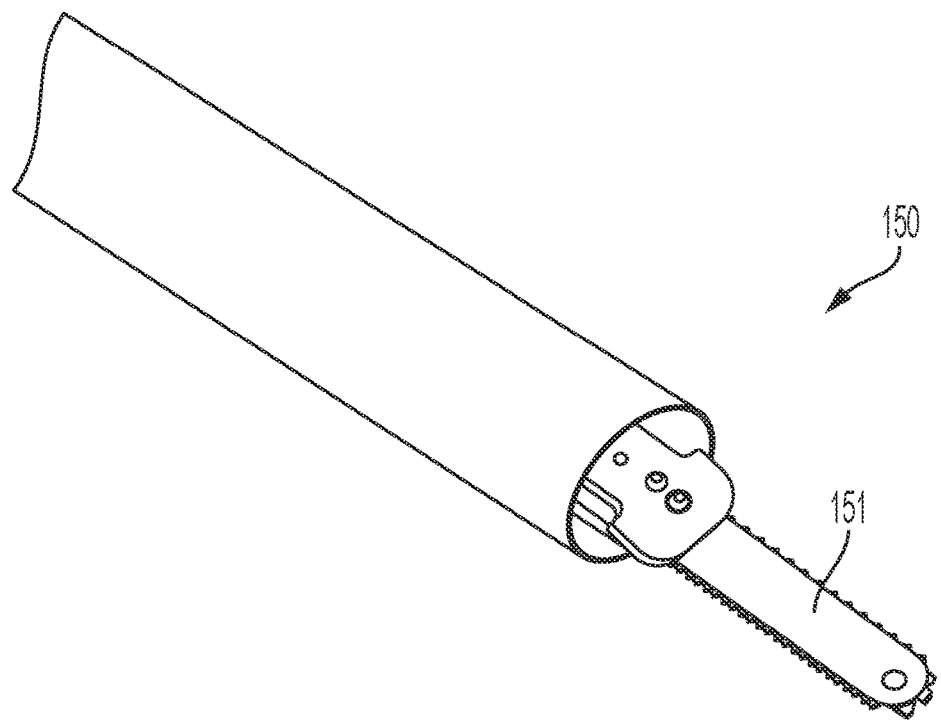
FIG. 20A shows an example embodiment of a chain saw with the saw blade in a horizontal position.
Figure 20B:
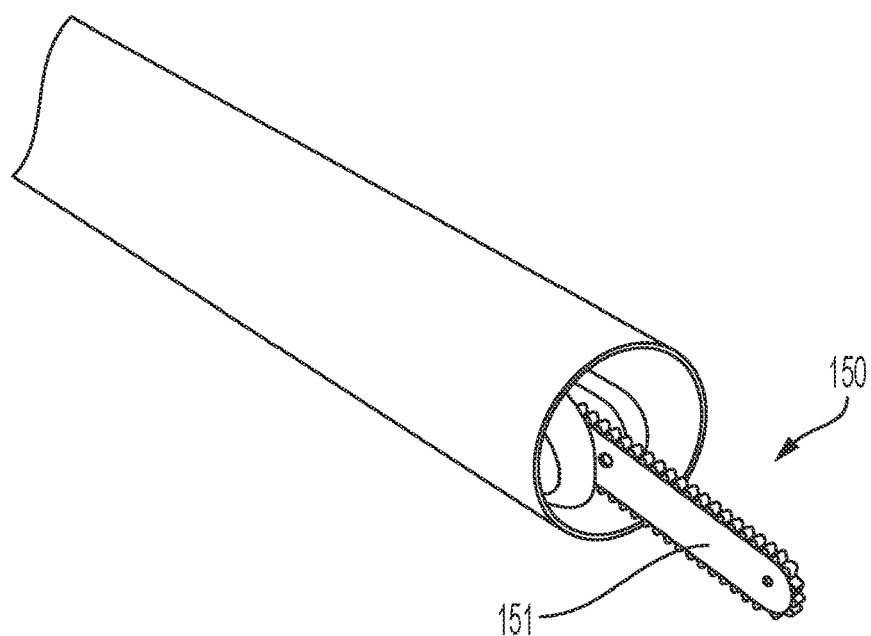
FIG. 20B shows the chain saw of FIG. 20A with the saw blade in a vertical position.
Figure 20C:
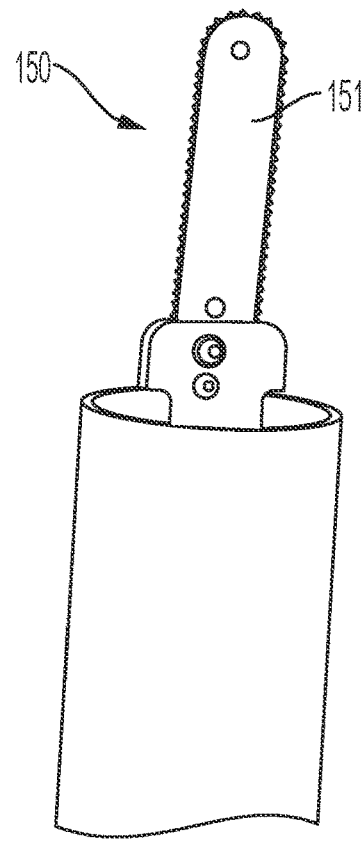
FIG. 20C shows a top view of the chain saw of FIG. 20A.
Figure 20D:
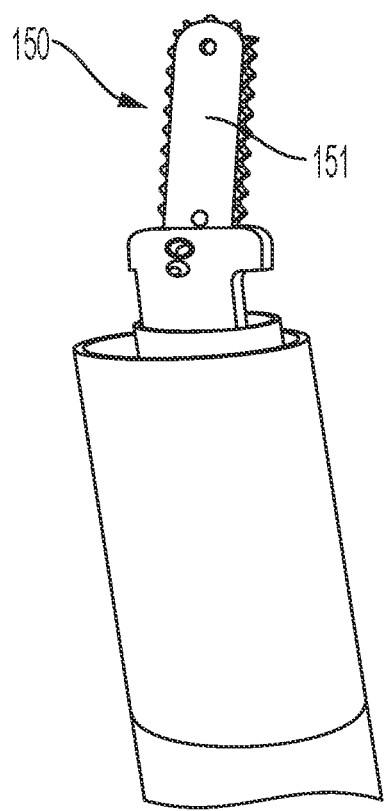
FIG. 20D shows the chain saw of FIG. 20A with the saw blade rotated slightly to the right.
Figure 20E:
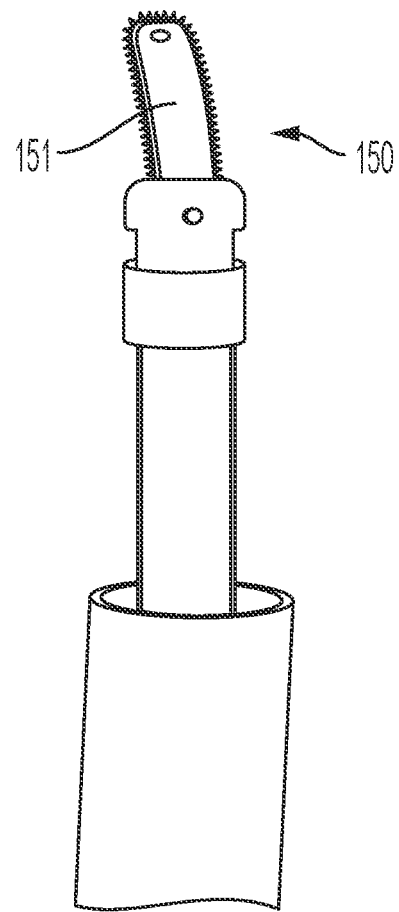
FIG. 20E shows the chain saw of FIG. 20A with the saw blade rotated slightly to the left.

FIGS. 20A-20E show an example embodiment of a chain saw 150. FIG. 20A shows the chain saw 150 with the saw blade 151 in a horizontal position. FIG. 20B shows the chain saw 150 with the saw blade 151 in a vertical position. FIG. 20C shows a top view of the chain saw 150. FIG. 20D shows the chain saw 150 with the saw blade 151 rotated slightly to the right. FIG. 20E shows the chain saw 150 with the saw blade 151 rotated slightly to the left.

Various methods may be used to manufacture chain saw links of embodiments disclosed herein. In accordance with the disclosure, a chain saw link, such as the chain saw link 40 shown in FIG. 2, may be manufactured by the following process.

First, the link is molded into its general shape by metal injection molding (MIM). Using metal injection molding, the links may be made in high volume at low cost. In metal injection molding, powdered metal and powdered plastic are mixed together (heated) and injected into a mold. At this point the molded parts are in a "green" state, having the generally molded shape but lower density than the final product. Through debinding and sintering processes, the parts are transformed to nearly 100% density metal components.

Figure 21:
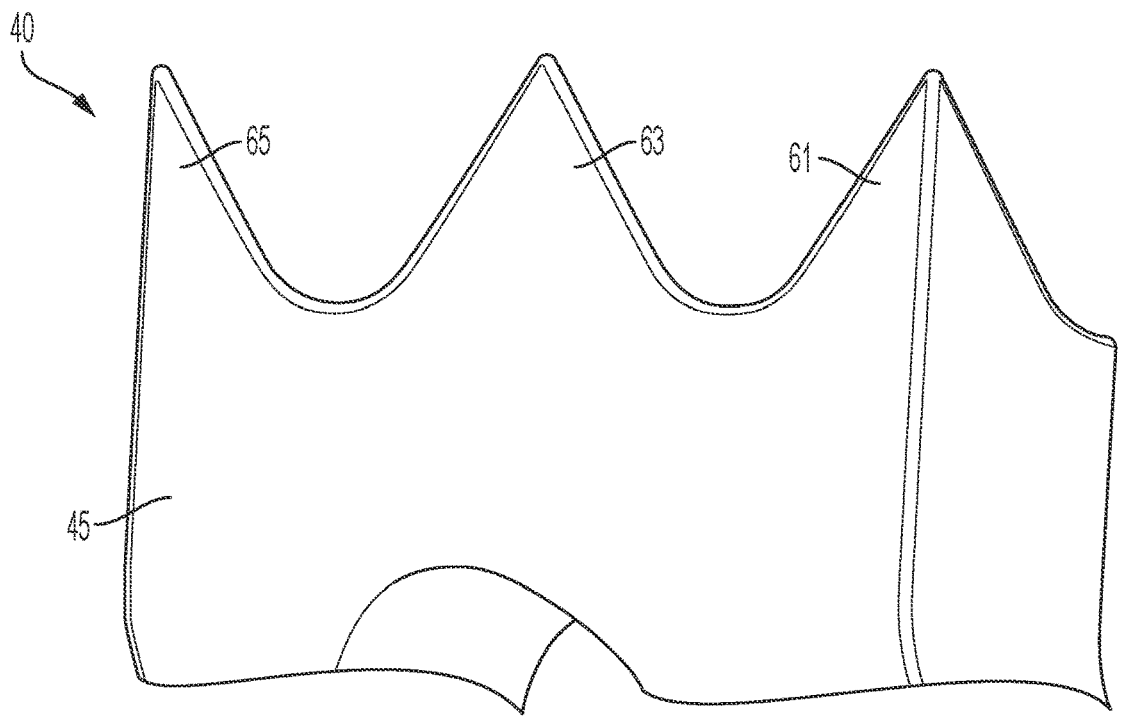
FIG. 21 shows a partial view of a chain saw link after a metal injection molding step.

FIG. 21 shows a partial view of the chain saw link 40 after the step of metal injection molding. Although a component may be molded with many fine features, it can be difficult to get a very sharp edge at this stage. As shown in FIG. 21, the leading and following cutting edges as well as the tops of each cutting tooth 61, 63, 65 are rounded. In the example shown in FIG. 21, the average radius of the edges is between 0.002 inches and 0.004 inches. Although this less than razor-sharp edge may be sufficient to cut bone, it may not be optimal for certain applications.

Figure 22A:
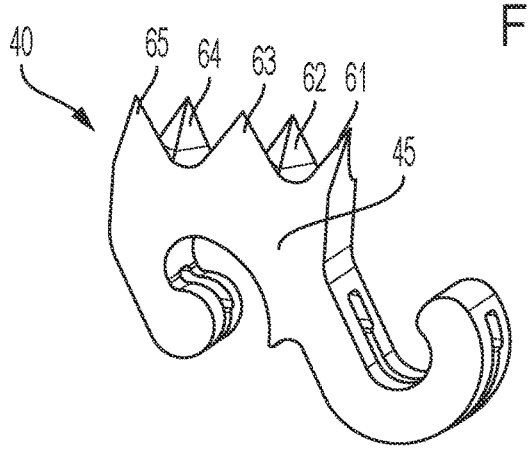
FIG. 22A shows a first lateral side of the chain saw link of FIG. 21.
Figure 22B:
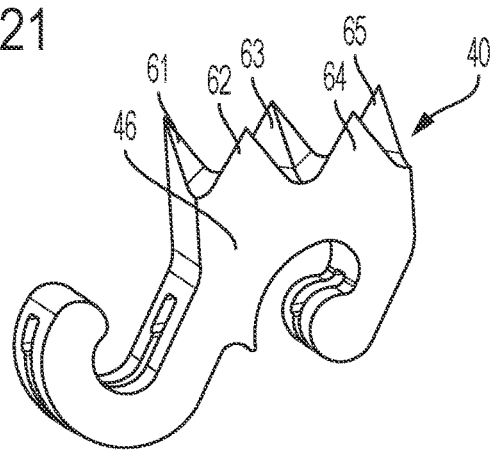
FIG. 22B shows a second lateral side of the chain saw link of FIG. 21.

FIGS. 22A and 22B show the first lateral side 45 and second lateral side 46 of the chain saw link 40 after molding but prior to a grinding step. The grinding will transform the bulbous tips and round edges to a ground cutting surface, leading to sharper cutting teeth 61, 62, 63, 64, and 65.

In accordance with the disclosure, after the chain saw links are molded, a grinding step is performed. The grinding step comprises double disc grinding. Through double disc grinding, very fine surface finishes can be produced, as can flat planar surfaces. The parallelism of the lateral sides 45, 46 of the link 40 can be precisely controlled, as can the thickness of the link 40. For example, the links 40 may be ground to a thickness (side-to-side) of 2 mm (0.078 inches).

Due to the unique configuration of the pyramid teeth in the example chain saw link 40, which have cutting edges aligned with the lateral sides 45, 46 of the link 40, the double disc grinding can sharpen and/or profile all necessary cutting edges. The combination of metal injection molding and the design of the teeth along with double disc grinding accomplishes the manufacture of the links with sharp teeth at an extremely low manufacturing price point.

In the double disc grinding process, two grinding discs are spaced apart and rotate opposite of each other as the chain saw links 40 are fed rotationally or linearly in the space between the rotating discs. The chain saw links 40 may be fed along a conveyor so that they pass continuously between the discs. One disc grinds the first lateral side 45 of the links 40 while the other disc grinds the second lateral side 46 of the links 40. This double disc grinding is an extremely efficient grinding process that uses abrasive wheels that oppose one another, grinding and removing equal amounts of material from both sides of a blank. The result provides flat surfaces, parallel sides, and smooth finishes. In one example, the process can yield parallel tolerances to 0.0005 inches and finishes to 16 Ra.

Figure 23:
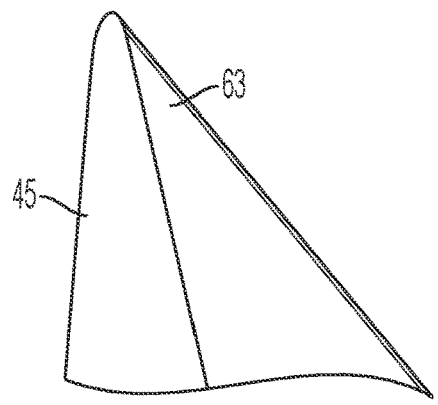
FIG. 23 shows an example cutting tooth of the chain saw link of FIG. 21 after a grinding step.

FIG. 23 shows the resultant sharp cutting edges and tips of the link, after grinding. An example cutting tooth 63 with sharp cutting edges is shown.

A further advantage of certain embodiments of chain saws disclosed herein is the ability to use the chain saws in robotic surgery. Surgical robots can be of great value in orthopedics because of their potential to make precise cuts regardless of conditions or skill of the surgeon. Current surgical robots with sagittal saws are subject to irregularities and inaccuracies because of the vibration of the sagittal saws. With embodiments as disclosed herein, the decrease in vibrations, reduced size of the saw blade, reduced cutting force, minimal deviation from intended cutting path (no skiving), reduced inaccuracies, and/or minimal heat production make the chain saw particularly well-suited for use in a robotic system. This is particularly true with surgical applications in which precise bone cuts are required.

In addition, sagittal saws are not designed to remove soft tissue (e.g., ligaments). Therefore, if soft tissue is introduced to the cutting field the saw must be removed and the soft tissue cut manually using regular surgical instruments. The bidirectional ability of some embodiments of this disclosure with asymmetric cutting elements allows bone cutting in one direction and soft tissue cutting in the other direction. Thus, robotic control of the saw can be continued through bone and soft tissue cutting without having to remove the robot saw.

A robotic control mechanism may be applied to guide the saw, such as a robotic controlled arm powered by a gear mechanism, cam, electromechanical, pneumatic, hydraulic, biological fluids or any combination or permutation thereof. The robotic control in some embodiments corrects automatically for bias in the direction opposite to the link travelling direction. The force required to resist the bias may be computed using a calculation of the amount of power being delivered to the saw. The resistive force may also be computed using input from other systems, for instance, optical systems such as laser systems or 3D visual systems, ultrasonic systems, Hall sensors, or sonar systems.

In some embodiments in accordance with this disclosure, a robotic system comprises at least one arm that is mechanically connected at one end to the patient's bone. The other end of the arm may be mechanically connected to an instrument, to a robotic arm, or to a computerized robot unit that includes a robotic arm.

The arm that is connected to the patient's bone, or a robotic arm to which it is connected, may carry, or may be configured to carry, an instrument, such as a bone saw and/or a cutting guide for a bone saw. For example, the arm connected to the patient's bone, or a robotic arm connected to it, may carry, or may be configured to carry, a chain saw as disclosed herein and/or a cutting guide for a chain saw as disclosed herein. Also, in some embodiments, other types of saws, e.g., sagittal saws, may be used. In other embodiments, the arm connected to the patient's bone, or a robotic arm to which it is connected, may carry a non-cutting instrument, including but not limited to a scanning probe, a temperature probe, a drug delivery system or device, or another instrument.

The arm of a robotic system as disclosed herein may be anchored to the patient's bone by a suitable support mount that can be affixed to the patient's bone. Support mounts for bones are known, such as for cutting guides. Other examples of support mounts that can be affixed to a patient's bone are shown and described in U.S. Provisional Patent Application No. 63/195,994, filed Jun. 2, 2021, entitled "Cutting Guide Systems and Methods." That patent application discloses support mounts that are suitable for fixation, for example, to a patient's tibia and/or femur.

The arm anchored to the patient's bone may be adjustable in six degrees of freedom: positioning along the x-y-z axes and rotational orientation with respect to the x-y-x axes. The arm may comprise one or more arm segments and/or one or more joints. The joint(s) may connect an arm segment to the support mount, an arm segment to an adjacent arm segment, and/or an arm segment to an instrument, robotic arm, or robot unit. The joint(s) may have any suitable construction allowing adjustment of the arm whereby the positioning and/or rotational orientation of the arm may be adjusted relative to the bone. Example joints include ball-and-socket joints, swivel joints, and hinge joints, among others.

In some embodiments, the arm connected to the patient's bone may have a feedback system whereby position and/or rotational orientation information may be transmitted to a control system. For example, the joints and/or arm segments may have transducers for reading position and/or rotational orientation information and connections (wireless or wired) for transmitting such information to the control system. The device thus provides a telemetry stream updating the robotic system as to the position and rotational orientation of the bone being resected. In this way, the position and/or rotational orientation of the bone relative to the robotic arm and/or instrument can be monitored and known at all times. The position and/or rotational orientation of the robotic arm and/or instrument can be automatically adjusted based upon the position and/or rotational orientation of the bone as determined from the feedback system.

In some embodiments, the arm(s) connected to the patient's bone may have one or more actuators, such as electromagnetic actuators (e.g., one or more stepper motors, servomotors, or other actuators), for moving the arm(s) into desired positions. The actuators(s) can adjust the position and/or rotational orientation of the arm(s). The actuator(s) can move the arm(s) at high or low speeds, can maintain the position of the instrument with respect to the bone, and can incorporate braking to lock the positioning if no real-time repositioning is needed.

In embodiments in which the arm that is connected to the patient's bone is attached at its other end to an instrument, adjusting the position and/or rotational orientation of the bone-connected arm in turn can adjust the position and/or rotational orientation of the instrument. Similarly, in embodiments in which the arm is attached directly to a robotic arm (as opposed to a floor-mounted robot unit that includes a robotic arm), the actuator(s) may be used to adjust the bone-connected arm in order to adjust the position and/or rotational orientation of the robotic arm. This in turn can adjust the position and/or rotational orientation of an instrument that is carried by the robotic arm.

In some example embodiments, an arm is connected at one end to a support mount that is affixed to the patient's bone and at the other end to a computerized robot unit that includes a robotic arm. The computerized robot unit may be mounted on the floor of the operating room. The bone-connected arm may be similar to an arm as described above. As the patient's bone moves relative to the robot unit, and thus relative to the robotic arm of the robot unit, the bone-connected arm provides feedback to the control system for the robot unit as to the position and/or orientation of the patient's bone relative to the robot unit, and thus relative to the robotic arm. The control system in turn can control the robotic arm, and any instrument carried by the robotic arm, based on the position and/or orientation of the patient's bone.

In some embodiments, an arm as described above may be attached to the patient's femur and/or to the patient's tibia. Separate arms may be attached, one to the patient's femur and one to the patient's tibia, whereby both arms are associated with the control system. The arm on the femur and the arm on the tibia could be used together for feedback of range of motion, positioning the knee joint in all planes and axes.

In some embodiments, one or more arms as described herein may be anchored to a patient's bone at one or more locations. For example, in one embodiment for attachment to a patient's femur, a first arm is anchored to the medial epicondyle, and a second arm is attached to the lateral epicondyle. The other ends of both arms may be connected to an instrument or to a robotic arm carrying an instrument. For example, an instrument or a robotic arm may be mounted between the two bone-connected arms. The attachment points of the bone-connected arms to the instrument or robotic arm may form an axis line about which the instrument or robotic arm may be rotated. The attachment points of the bone-connected arms to the two epicondyles may form an axis line between them about which the structure (the two bone-connected arms and the instrument or robotic arm) may be rotated. This can position the robotic arm or instrument for various cuts desired for the femur. The whole assembly may be moveable by actuators as described above to move the robotic arm or instrument into the various desired positions.

In some embodiments, wherein an instrument or a robotic arm carrying an instrument is directly attached to one or more arms that are in turn attached to the patient's bone (such as the arms described above attached to the medial and lateral epicondyles), the instrument or robotic arm can be supported by the bone-connected arm(s) without the need for a floor-mounted robot unit as used in prior art systems. The devices in such examples may be mounted exclusively on the patient, and thus may move with the patient's movement.

Figure 24:
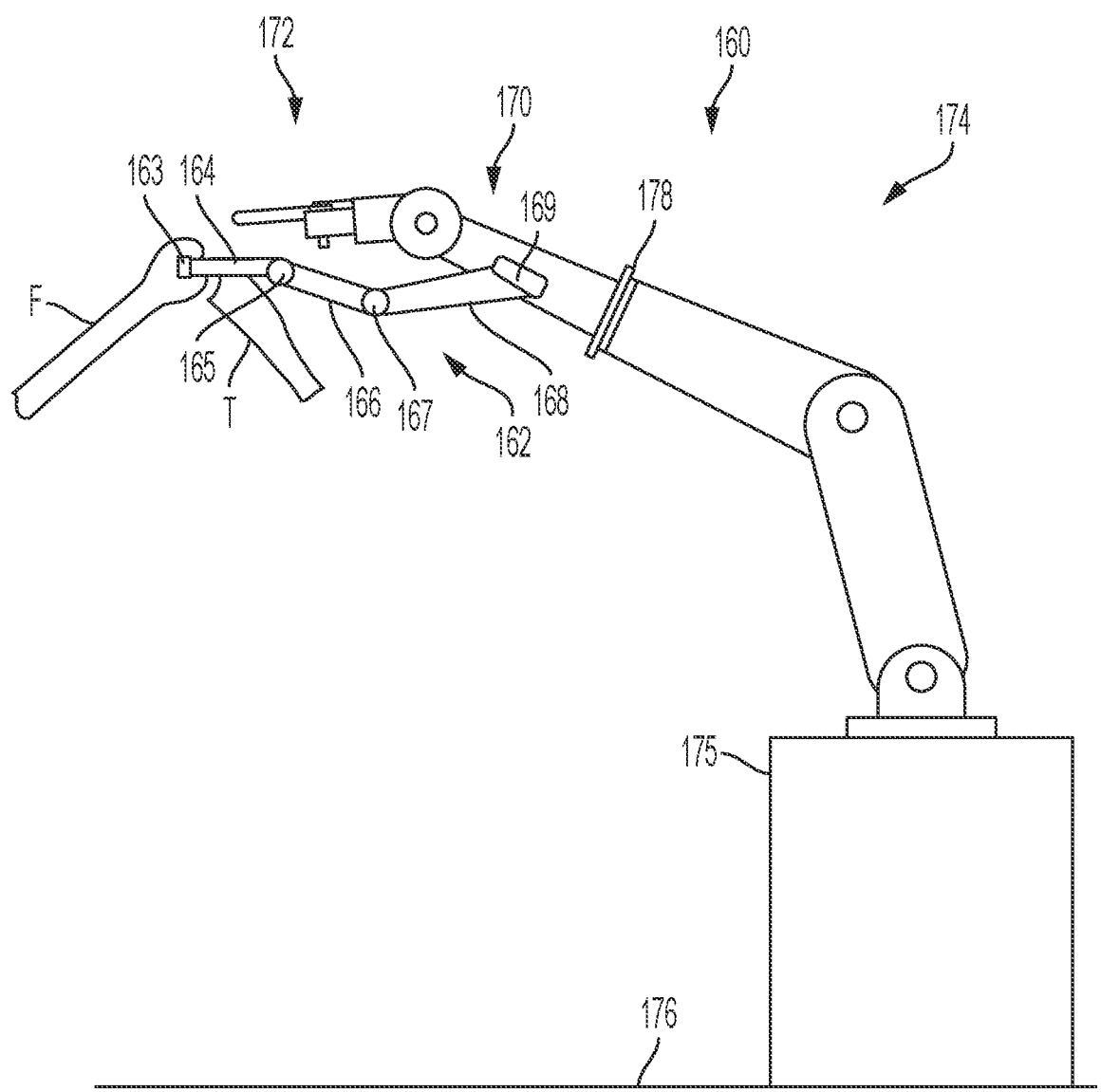
FIG. 24 shows an example of a robotic system for surgical use comprising an arm connected to a bone of a patient.

FIG. 24 shows an example of robotic system 160 for surgical use comprising an arm 162 connected to a bone of a patient, such as a femur F. The arm 162 may additionally or alternatively be attached to a tibia T. In the illustrated embodiment, a first end of the arm 162 is connected to the bone F at a joint 163, allowing motion in all directions and rotational orientations. The arm 162 comprises a series of arm segments 164, 166, 168. The arm segment 164 is connected to the arm segment 166 by a joint 165, allowing relative motion between them. The arm segment 166 is connected to the arm segment 168 by a joint 167, allowing relative motion between them. A second end of the arm 162 is connected to a robotic arm 170 at a joint 169, allowing relative motion between the bone-connected arm 162 and the robotic arm 170. The robotic arm 170 carries an instrument 172 (e.g., bone saw, guide for bone saw, or other instrument). The robotic arm 170 may be part of a robot unit 174, which may include a base unit 175 on the floor 176 of an operating room. In an alternative embodiment, the second end of the arm 162 may be directly connected to an instrument 172 without the intermediate robotic arm 170, such that the arm 162 serves as a robotic arm that controls positioning of the instrument 172. In another alternative embodiment, the robotic arm 170 is not part of a floor-mounted robot unit but instead is fully supported by the arm 162. Thus, the structure below point 178 on the robotic arm 170 may be omitted (the electronics of the base unit 175 may be incorporated in the robotic arm 170).

The arm 162 connected to the patient's bone may have a feedback system whereby position and/or rotational orientation information may be transmitted to a control system of the robotic system 160. For example, the joints 163, 165, 167, 169 and/or arm segments 164, 166, 167 may have transducers for reading position and/or rotational orientation information and connections (wireless or wired) for transmitting such information to the control system. The control system can use the information to adjust the position of the arm 162, the robotic arm 170, and/or the instrument 172. In some embodiments, the arm 162 connected to the patient's bone may have one or more actuators, such as electromagnetic actuators (e.g., one or more stepper motors, servomotors, or other actuators), for moving the arm 162 into desired positions.

Figure 25:
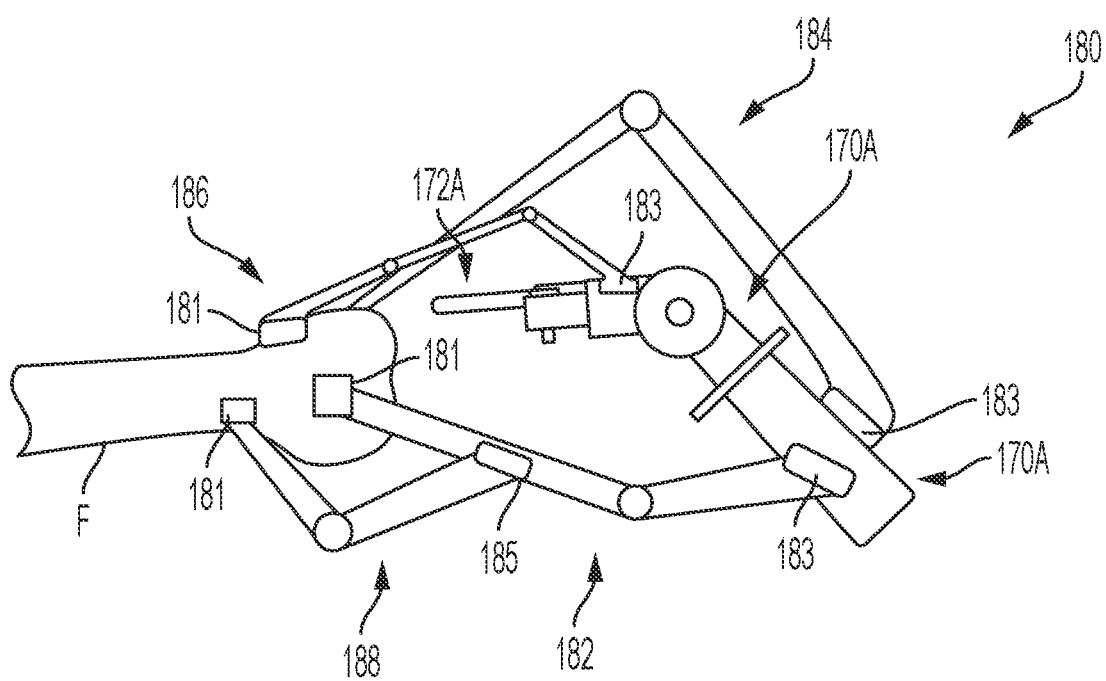
FIG. 25 shows another example of a robotic system for surgical use comprising multiple arms connected to a bone of a patient.

FIG. 25 shows another example of robotic system 180 for surgical use comprising a plurality of arms 182, 184, 186, 188 connected to a bone of a patient, such as a femur F. A first end of each arm 182, 184, 186, 188 is connected to the bone at a joint 181, allowing motion in all directions and rotational orientations. Each arm 182, 184, 186, 188 may comprise multiple arm segments connected together by one or more joints, allowing relative motion between them. A second end of each arm 182, 184, 186 is connected to a robotic arm 170A at a joint 183, allowing relative motion between them. A second end of arm 188 is connected to the arm 182 and through the arm 182 to the robotic arm 170A. The second end of arm 188 is connected to the arm 182 at a joint 185, allowing relative motion between them. The robotic arm 170A carries an instrument 172A. In the illustrated embodiment, the robotic arm 170A is not part of a floor-mounted robot unit but instead is fully supported by the arms 182, 184, 186, 188. In an alternative embodiment, the robotic arm 170A may be part of a robot unit, which may be on the floor of an operating room. In another alternative embodiment, the second ends of the arms 182, 184, 186 may be connected directly to an instrument 172A, such that the arms 182, 184, 186, 188 function as robotic arms that control positioning of the instrument 172A.

The arms 182, 184, 186, and/or 188 connected to the patient's bone may have a feedback system whereby position and/or rotational orientation information may be transmitted to a control system of the robotic system 180. For example, the joints and/or arm segments may have transducers for reading position and/or rotational orientation information and connections (wireless or wired) for transmitting such information to the control system. The control system can use the information to adjust the position of the arms 182, 184, 186, 188, the robotic arm 170A, and/or the instrument 172A. In some embodiments, the arms 182, 184, 186, 188 connected to the patient's bone may have one or more actuators, such as electromagnetic actuators (e.g., one or more stepper motors, servomotors, or other actuators), for moving the arms 182, 184, 186, and/or 188 into desired positions.

Like the arm 188 in FIG. 25, a robotic system in accordance with the disclosure may have arms that connect to other arms, forming a branched system between the bone and the instrument or robotic arm carrying the instrument. This can help with the stability and fine positioning of the device.

Devices as disclosed herein can achieve one or more advantages. For example, certain embodiments as described herein can give direct feedback as to the position and/or orientation of the patient's bone (e.g., femur and/or tibia) more directly than the optical systems presently used. Certain embodiments as disclosed herein also can have less latency between patient movement and robotic arm response, therefore yielding a smoother and safer control of the saw blade or other instrument. Certain embodiments as disclosed herein can be much more accurate with much less equipment and software, especially since devices as disclosed herein do not require the computer processing power that is needed for stereotaxic systems that use stereo cameras and covert images into location and rotational orientation information. Certain embodiments as disclosed herein can be less expensive and/or less complex than prior systems and can take up less room than prior systems. Certain embodiments as disclosed herein can keep the attachments and the saw control very close to the structural components of the robot, inherently yielding stability, accuracy, and reliability.

In certain embodiments, the mechanical connection of the instrument or robotic arm to the bone through the bone-connected arm(s) (and in some embodiments the robot unit) results in greater stability during the procedure. In other words, in a knee surgery example, the system can stabilize the patient's knee that is being loaded by the cutting action.

In sum, certain embodiments as disclosed herein can achieve one or more advantages, such as lower cost, easier use, less failure, more precise cuts, lower procedure time, lower recovery time, and/or better outcomes.

In other variations of robotic or automated systems (with or without bone-connected arm(s) as described above), a saw (e.g., chain saw) can be connected to a feedback system that measures one or more of the various conditions in cutting the bone (e.g., cutting or other forces, rotational force, the various forces against the links, the forces against the bar, the forces against the drive pin, the forces within the gears, the levels of vibration, the pitch and volume of noise, and/or the amount of deflection from the ideal plane). These measurements are then analyzed by software to provide intelligent control of the saw, driver, and/or robot.

For example, bone is heterogeneous with varying degrees of density, hardness, and dryness, among other characteristics. Saws perform differently against different types of bone in terms of speed, vibration, noise (pitch and volume), and ability to hold a plane. A bone saw needs to be able to cut the bone safely, without endangering the soft tissues surrounding the bone.

As an example of using the feedback system, based on the measurements, the cutting system can determine whether the saw is employed against hard bone, soft bone, or soft tissue. As the saw moves through soft cancellous bone and hits the hard cortical bone, the control system identifies the harder bone and can determine if the saw is approaching or engaging the edge of bone in the cutting zone, beyond which are delicate soft tissues, such as the medical cruciate ligament and, on the other side, the lateral cruciate ligament. Based on the measurements and software analysis, the control system can control the speed of the saw to cut faster or slower and/or move to an oscillating mode, in order to protect soft tissue. The control system could stop the saw immediately upon cutting through the bone (recognizing that the forces against the saw were reduced dramatically) before it hurts any soft tissue.

Figure 26:
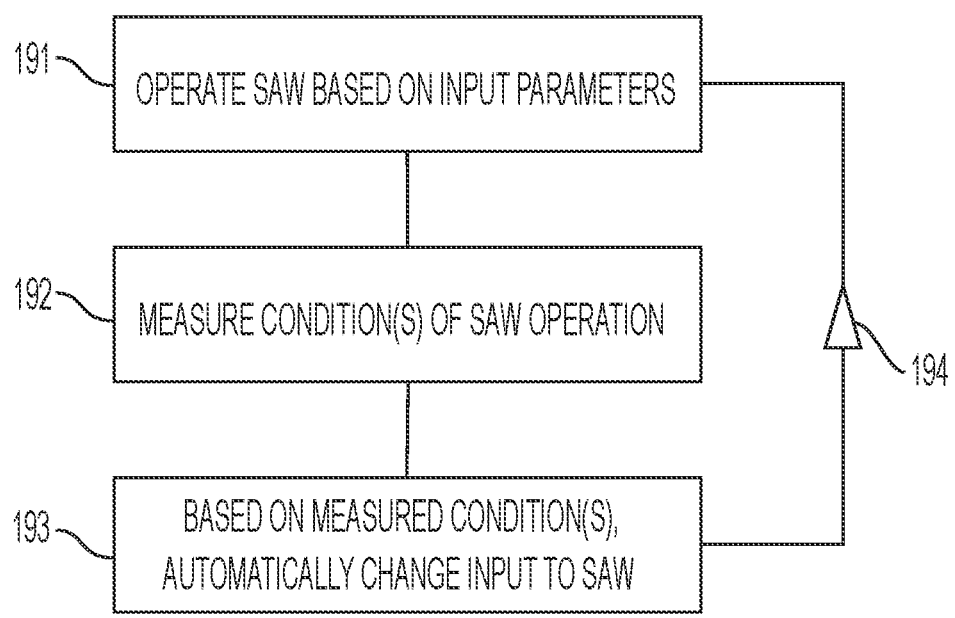
FIG. 26 is a flow chart of an example method of automated control of a saw.

FIG. 26 is a flow chart of an example method of automated control of a saw. An example automated system for surgical use comprises a saw, such as a chain saw for cutting bone, a feedback system that measures one or more conditions of the chain saw while the chain saw is operating, and a control system that receives information from the feedback system and based on that feedback automatically changes an input to the chain saw to change the operation of the chain saw. In a first step 191, the saw is operated based upon operating parameters sent to the saw. In a second step 192, the feedback system measures one or more conditions of the saw while the saw is operating. For example, the feedback system may measure one or more forces or other conditions such as vibration, noise, and/or deflection, as described above. The feedback system sends these signals to the control system. In a third step 193, the control system receives information from the feedback system and based on that feedback automatically changes an input to the saw to change the operation of the saw. For example, the control system may change an input to the saw to change its speed or manner or direction of movement (e.g., reverse direction of a chain and/or switch between single direction mode and oscillating mode). The input from the control system based on information from the feedback system is shown as line 194 in FIG. 26. The process may be repeated continuously or as desired to continue automatically updating the operation of the saw based on the feedback.

In addition to cutting bone for implants, such as knee implants, spinal implants, and other implants, embodiments of chain saws disclosed herein may be used for other procedures involving bone or tissue cutting. For example, embodiments of chain saws disclosed herein may be used for cutting bone to join bone, to correct a condition, or for other purposes. Thus, the use of chain saws as disclosed herein is not limited to total knee or total implant arthroplasty. The use of chain saws as disclosed herein is not limited to use with a guidance system. Chain saws as disclosed herein may be used in a number of procedures in which precise bone or tissue cutting is advantageous.

As an example, embodiments of chain saws disclosed herein may be used to fuse a spine. The chain saw may be used to make parallel cuts of adjacent vertebral bodies, removing the disc between them, and joining the two flat surfaces of the natural human bone together. The precise cutting produces a very stable junction where the mating bones have the opportunity to migrate and morph into one unified bone. Embodiments of chain saws disclosed herein may also be used to excise bone that could contain disease such as a tumor or some other deformity. An example of this would be a foot or toe condition like a hammertoe condition, such as with the large toe facing towards the midline of the foot, a condition that can arise from wearing high heels. Embodiments of chain saws disclosed herein can be used to make one or more cuts to realign the toe to a more natural position.

Advantages of certain embodiments of chain saws disclosed herein over prior art oscillating sagittal saws include the ability to operate the cutting teeth continuously without reversing direction as well as the ability to operate the cutting teeth in a linear direction across the surface to be cut. Prior art bone cutting sagittal saws typically oscillate around a pivot axis through a small angle, such that the cutting surface of the saw moves back and forth against the bone as well as in an arc against the bone. By contrast, with embodiments of chain saws as disclosed herein, the links can be moved continuously around the saw bar without reversing direction and can move in a linear direction along the longitudinal sides of the saw bar. For example, with plunge or other cuts, the chain can be operated in a continuous direction around the saw bar without reciprocating, presenting continuous non-reciprocating cutting motion on the longitudinal sides and distal end of the saw bar. In addition, when a longitudinal side of the chain saw is presented against the surface to be cut, the links and their cutting teeth can be operated in a continuous linear direction across the surface being cut. When the cutting elements have cutting edges that facilitate slicing the bone or other tissue, such as the pyramid-shaped teeth described above, the chain saw enables a continuous slicing action through the bone or other tissue. The ability to combine continuous cutting action without reversing direction and/or in a linear direction with cutting teeth having shapes as described herein to achieve a continuous slicing action as the primary cutting method provides unique advantages compared to prior art saws.

A further advantage to certain embodiments of chain saws disclosed herein is the ability to operate the chain saws at low operating speeds. In certain embodiments, the chain saw can be run at low speed while still creating a bite or edge or footing in bone, even on a slanted or irregular surface. This is a significant advantage over current sagittal saws, which in virtually all cases must be run at high speed to begin the cut.

A further advantage to certain embodiments of chain saws disclosed herein is the miniaturization that is achievable with the disclosed designs, facilitating utility in certain surgical applications. The designs of the saw bars and links result in chain saws that can be made at sufficiently small sizes to operate safely, reliably, and effectively.

Many variations of the above-described embodiments are possible while still retaining one or more features of the invention. For example, links in a single chain may take different shapes. For example, a first type of link may have hooks on both ends, a second type of link may have recesses on both ends, and the first type of links may alternate with the second type of links in the chain. Components of the chain saw, including the links and saw bar, may be made of any suitable materials, including metal (e.g., stainless steel), plastic, composite, ceramic, carbon, or carbon fiber materials. Some of these materials, e.g., biocompatible ceramics, can lead to reduced debris as well as reduced heat and can minimize galling.

Inventions as disclosed herein may be practiced together or separately. For example, a chain saw with links have cutting teeth with features as disclosed herein, such as the pyramidal shape and/or arrangement in rows along lateral sides, may be used with different saw bars, such as a saw bar with a channel or a gutter as in FIG. 11B and without a rail as in FIGS. 5A-5C. As another example, a saw bar with a rail as in FIGS. 5A-5C may be used with links having grooves as disclosed herein but with different cutting teeth than those disclosed herein.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A chain saw comprising:
   a saw bar having a first longitudinal side, a second longitudinal side, and a distal end, wherein the first longitudinal side, the second longitudinal side, and the distal end define at least part of a chain path that extends in a chain path direction around the saw bar; and
   a plurality of links arranged in a chain along the chain path around the saw bar;
   wherein the saw bar comprises a main body and a rail extending from the main body along at least part of the chain path;
   wherein each of the links in the plurality of links comprises a groove such that the links straddle the rail of the saw bar;
   wherein each of the links in the plurality of links comprises a bottom surface, with a first part of the bottom surface on one side of the groove and with a second part of the bottom surface on an opposite side of the groove;
   wherein the main body of the saw bar comprises a first ledge extending beyond a first side of the rail and a second ledge extending beyond a second side of the rail, wherein a width of the rail in a direction perpendicular to the chain path direction is narrower than a width of the main body of the saw bar in the direction perpendicular to the chain path direction at an area of the ledges; and
   wherein the links are positionable on the saw bar such that the first part of the bottom surface of each link contacts the first ledge of the main body of the saw bar on the first side of the rail and the second part of the bottom surface of each link contacts the second ledge of the main body of the saw bar on the second side of the rail, such that forces on the links are transferred to the ledges of the saw bar on either side of the rail, and a clearance is present between the link and a top of the rail such that no part of the link contacts the top of the rail.

2. The chain saw as recited in claim 1, wherein the rail of the saw bar comprises a projection and the grooves of the links comprise notches accommodating the projection, and wherein the projection restrains the links from dislocation in a direction away from the saw bar.

3. The chain saw as recited in claim 1, wherein a first link of the plurality of links comprises a hook that engages a recess of a second link of the plurality of links, thereby coupling the first link and the second link and allowing the first link and the second link to articulate with respect to each other without decoupling as the chain is driven around the saw bar.

4. The chain saw as recited in claim 3, wherein at least one link of the first link and the second link comprises a plurality of pyramidal cutting teeth.

5. The chain saw as recited in claim 3, wherein at least one link of the first link and the second link comprises a first row of pyramidal cutting teeth along a first lateral side of the at least one link and a second row of pyramidal cutting teeth along a second lateral side of the at least one link.

6. The chain saw as recited in claim 5, wherein the cutting teeth along the first lateral side of the at least one link are staggered with respect to the cutting teeth along the second lateral side of the at least one link, such that a peak along the first lateral side is aligned with a valley along the second lateral side.

7. The chain saw as recited in claim 3, wherein the first link has a first pyramidal cutting tooth having a first profile and a second pyramidal cutting tooth at an edge of the first link having a second profile that is half the size of the first profile, and wherein the second link is adjacent to the first link and has a third pyramidal cutting tooth having a profile that is half the size of the first profile, wherein when the chain is assembled on the saw bar, the third pyramidal cutting tooth of the second link is positioned next to the second pyramidal cutting tooth of the first link.

8. The chain saw as recited in claim 1, wherein a first link of the plurality of links comprises a hook that engages a recess of a second link of the plurality of links, thereby coupling the first link and the second link and allowing the first link and the second link to articulate with respect to each other without decoupling as the chain is driven around the saw bar; and
   wherein at least one link of the first link and the second link comprises a cutting tooth in the shape of a cone or pyramid.

9. The chain saw as recited in claim 8, wherein the cutting tooth is in the shape of an oblique pyramid.

10. The chain saw as recited in claim 8, wherein a peak of the cutting tooth is aligned with a lateral side of the at least one link.

11. A chain saw comprising:
a saw bar having a first longitudinal side and a second longitudinal side, wherein the first longitudinal side and the second longitudinal side define at least part of a chain path that extends in a chain path direction around the saw bar; and
a plurality of links arranged in a chain along the chain path around the saw bar;
wherein the saw bar comprises a main body and a rail extending from the main body along at least part of the chain path;
wherein the rail has a first lateral side, a second lateral side, and a top, wherein a width of the rail from the first lateral side of the rail to the second lateral side of the rail in a direction perpendicular to the chain path direction is narrower than a width of the main body of the saw bar in the direction perpendicular to the chain path direction;
wherein each of the links in the plurality of links comprises a groove such that the links straddle the rail of the saw bar;
wherein each of the links in the plurality of links comprises a bottom surface, with a first part of the bottom surface on one side of the groove and with a second part of the bottom surface on an opposite side of the groove;
wherein a link in the plurality of links is positionable on the saw bar such that the first part of the bottom surface of the link contacts a first ledge of the main body of the saw bar on a first side of the rail, the second part of the bottom surface of the link contacts a second ledge of the main body of the saw bar on a second side of the rail, and a clearance is present between the link and the top of the rail such that no part of the link contacts the top of the rail.

12. The chain saw as recited in claim 11, wherein when said link in the plurality of links is positioned on the saw bar, the clearance that is present between said link and the top of the rail is between a top end of the groove of said link and the top of the rail.

13. The chain saw as recited in claim 11, wherein the rail of the saw bar comprises a projection and the grooves of the links comprise notches accommodating the projection, and wherein the projection restrains the links from dislocation in a direction away from the saw bar.

14. The chain saw as recited in claim 13, wherein when the links are arranged around the saw bar, a clearance is present between a bottom of the projection of the rail and a bottom of the notch of the groove of each of the links in the plurality of links.

15. The chain saw as recited in claim 11, wherein a width of the groove of each of the links in the plurality of links is wider than a width of the rail.

16. The chain saw as recited in claim 11, wherein a first link of the plurality of links comprises a hook that engages a recess of a second link of the plurality of links, thereby coupling the first link and the second link and allowing the first link and the second link to articulate with respect to each other without decoupling as the chain is driven around the saw bar.

17. A chain saw comprising:
a saw bar having a first longitudinal side, a second longitudinal side, and a distal end, wherein the first longitudinal side, and the second longitudinal side, and the distal end define at least part of a chain path that extends in a chain path direction around the saw bar; and
a plurality of links arranged in a chain along the chain path around the saw bar;
wherein the saw bar comprises a main body and a rail extending from the main body along at least a part of a cutting portion of the chain path that is configured to be used for cutting;
wherein each of the links in the plurality of links comprises a groove such that the links straddle the rail of the saw bar;
wherein each of the links in the plurality of links comprises a bottom surface, with a first part of the bottom surface on one side of the groove and with a second part of the bottom surface on an opposite side of the groove;
wherein the main body of the saw bar comprises a first ledge extending beyond a first side of the rail and a second ledge extending beyond a second side of the rail, wherein a width of the rail in a direction perpendicular to the chain path direction is narrower than a width of the main body of the saw bar in the direction perpendicular to the chain path direction at an area of the ledges;
wherein a link in the plurality of links is positionable on the saw bar along at least said part of the cutting portion of the chain path such that the first part of the bottom surface of the link contacts the first ledge of the saw bar, and the second part of the bottom surface of the link contacts the second ledge of the saw bar, and a clearance is present between the link and a top of the rail such that no part of the link contacts the top of the rail.

18. The chain saw as recited in claim 17, wherein when the links are arranged around the saw bar, the clearance is present between the top of the rail and a top end of the groove of each of the links in the plurality of links.

19. The chain saw as recited in claim 17, wherein the rail of the saw bar comprises a projection and the grooves of the links comprise notches accommodating the projection, and wherein the projection restrains the links from dislocation in a direction away from the saw bar.

20. The chain saw as recited in claim 19, wherein when the links are arranged around the saw bar, a clearance is present between a bottom of the projection of the rail and a bottom of the notch of the groove of each of the links in the plurality of links.

21. The chain saw as recited in claim 17, wherein a width of the groove of each of the links in the plurality of links is wider than a width of the rail.

22. The chain saw as recited in claim 17, wherein a first link of the plurality of links comprises a hook that engages a recess of a second link of the plurality of links, thereby coupling the first link and the second link and allowing the first link and the second link to articulate with respect to each other without decoupling as the chain is driven around the saw bar.

23. The chain saw as recited in claim 17, wherein when the link in the plurality of links is positioned on saw bar, the link is free to move off of the ledges of the main body of the saw bar in a direction away from the main body of the saw bar, perpendicular to the chain path direction.

* * * * *